(12) United States Patent
Tan et al.

(10) Patent No.: US 10,179,178 B2
(45) Date of Patent: Jan. 15, 2019

(54) NANOPARTICULATE CONTRAST AGENT

(71) Applicant: NANYANG TECHNOLOGICAL UNIVERSITY, Singapore (SG)

(72) Inventors: Thatt Yang Timothy Tan, Singapore (SG); Yan Zhang, Singapore (SG)

(73) Assignee: NANYANG TECHNOLOGY UNIVERSITY, Singapore (SG)

( * ) Notice: Subject to any disclaimer, the term of this patent is extended or adjusted under 35 U.S.C. 154(b) by 0 days.

(21) Appl. No.: 14/423,994

(22) PCT Filed: Aug. 27, 2013

(86) PCT No.: PCT/SG2013/000372
§ 371 (c)(1),
(2) Date: Feb. 25, 2015

(87) PCT Pub. No.: WO2015/035341
PCT Pub. Date: Mar. 6, 2014

(65) Prior Publication Data
US 2015/0182641 A1 Jul. 2, 2015

Related U.S. Application Data

(60) Provisional application No. 61/693,371, filed on Aug. 27, 2012.

(51) Int. Cl.
| | | |
|---|---|---|
| A61K 49/18 | (2006.01) | |
| A61K 49/00 | (2006.01) | |
| A61K 49/06 | (2006.01) | |
| B82Y 5/00 | (2011.01) | |
| B82Y 30/00 | (2011.01) | |

(52) U.S. Cl.
CPC ........ *A61K 49/183* (2013.01); *A61K 49/0002* (2013.01); *A61K 49/0019* (2013.01); *A61K 49/0093* (2013.01); *A61K 49/06* (2013.01); *A61K 49/1818* (2013.01); *B82Y 5/00* (2013.01); *B82Y 30/00* (2013.01)

(58) Field of Classification Search
None
See application file for complete search history.

(56) References Cited

U.S. PATENT DOCUMENTS

2005/0025971 A1* 2/2005 Cho ............... A61K 47/48861
428/403
2006/0275927 A1 12/2006 Dubin
2011/0200534 A1 8/2011 Cheon et al.

FOREIGN PATENT DOCUMENTS

| WO | 1996/023879 | 8/1996 |
| WO | 2001/004144 | 1/2001 |
| WO | 2003/029462 | 4/2003 |
| WO | 2011/150212 | 12/2011 |

OTHER PUBLICATIONS

Zhang et al. Shape, size, and phase-controlled rare-earth fluoride nanocrystals with optical up-conversion properties. 2009 Chem. Eur. J. 15: 11010-11019.*
Budijono et al. Synthesis of stable block-copolymer-protected NaYF4:Yb3+, Er+ up-converting phosphor nanoparticles. 2010 Chem. Mater. 22: 311-318.*
Qian et al. Synthesis of hexagonal-phase core-shell NaYF4 nanocrystals with tunable upconversion fluorescence. 2008 Langmuir 24: 12123-12125.*
Mahalingam et al. Preferential suppression of high-energy upconverted emissions of Tm3+ by Dy3+ ions in Tm3+/Dy3+/Yb3+-doped LiYF4 colloidal nanocrystals. 2011 Chem. Commun. 47: 3481-3483. Published online Feb. 9, 2011.*
Zhang et al. Shape, size, and phase-controlled rare-Earth fluoride nanocrystals with optical up-conversion properties. 2009 Chemistry 15: 11010-11019.*
Mi et al. Multifunctional nanocomposites of superparamagnetic (Fe3O4) and NIR-responsive rare earth-doped up-conversion fluorescent (NaYF4 : Yb,Er) nanoparticles and their applications in biolabeling and fluorescent imaging of cancer cells. 2010 Nanoscale 2: 1141-1148.*
Written Opinion of the International Searching Authority dated Nov. 4, 2013 for PCT/SG2013/000372.
International Preliminary Report on Patentability (Ch. II of the Patent Cooperation Treaty) dated Oct. 9, 2014 for PCT/SG2013/000372.
Kim, J.; Piao, Y.; Hyeon, T. "Multifunctional nanostructured materials for multimodal imaging, and simultaneous imaging and therapy" *Chem. Soc. Rev.* 2009, 38, pp. 372-390.
Louie, A. "Multimodality Imaging Probes: Design and Challenges" *Chemical Review* 2010, 110, pp. 3146-3195.
Nahrendorf, M., Sosnovik, D. E., Weissleder, R. "MR-optical imaging of cardiovascular molecular targets" *Basic Research in Cardiology* 2008, 103, pp. 87-94.
Prinzen, L., Miserus, Robbert-Jan J. H. M., Dirksen, Anouk, Hackeng, Tilman M., Deckers, Niko, Bitsch, Nicole J., Megens,, Douma, Kim, Heemskerk, Johan W., Kooi, M. Eline, Frederik, Peter M., Slaaf, Dick W., van Zandvoort, Marc A. M. J., Reutelingsperger, Chris P. M. "Optical and Magnetic Resonance Imaging of Cell Death and Platelet Activation Using Annexin A5-Functionalized Quantum Dots" *Nano Letters* 2006/2007, 7, pp. 93-100.
Frullano, L.; Meade, T. J. "Multimodal MRI contrast agents" *J. Biol. Inorg. Chem.* 2007, 12, pp. 939-949.
Basilion, J. P., Yeon, S., Botnar R. "Magnetic Resonance Imaging: Utility as a Molecular Imaging Modality" *Current Topics in Development Biology* 2005, 70, pp. 1-33.

(Continued)

*Primary Examiner* — Michael G. Hartley
*Assistant Examiner* — Jennifer Lamberski
(74) *Attorney, Agent, or Firm* — Ladas & Parry, LLP

(57) ABSTRACT

Provided is a nanoparticulate composite with two layers. One of the layers comprises one or more metals, which are a paramagnetic metal, a ferromagnetic metal, or a superparamagnetic metal. This layer also contains one or more suitable dopants. The other layer comprises one or more metals of gadolinium, manganese (II), and iron (III), in the form of an oxide or a fluoride. This layer may contain one or more lanthanide dopants. The nanoparticulate composite may be used as a contrast agent, in particular in magnetic resonance imaging.

15 Claims, 7 Drawing Sheets

(56) References Cited

OTHER PUBLICATIONS

Sharma, P., Brown, S., Walter, G., Santra, S., Moudgil, B. "Nanoparticles for bioimaging" *Advances in Colloid and Interface Science* 2006, 123-126, pp. 471-485.

Shen, J., Sun, L. D., Yan, C. H. "Luminescent rare earth nanomaterials for bioprobe applications" *Dalton Transactions* 2008, 5687, pp. 5687-5697.

Jennings, L. E.; Long, N. J. "'Two is better than one'—probes for dual-modality molecular imaging" *Chemical Communications* 2009, 24, pp. 3511-3524.

Blé, F.-X.; Schmidt, P.; Cannel, C.; Kneuer, R.; Karmouty-Quintana, H.; Bergmann, R.; Coote, K.; Danahay, H.; Zurbruegg, S.; Gremlich, H.-U.; Beckmann, N. "In Vivo Assessments of Mucus Dynamics in the Rat Lung Using a Gd-Cy5.5-Bilabeled Contrast Agent for Magnetic Resonance and Optical Imaging" *Magn. Reson. Med.* 2009, 62, pp. 1164-1174.

Li, Z.; Zhang, Y.; Shuter, B.; Muhammad Idris, N. "Hybrid Lanthanide Nanoparticles with Paramagnetic Shell Coated on Upconversion Fluorescent Nanocrystals" *Langmuir* 2009, 25, pp. 12015-12018.

Wang, D.; He, J.; Rosenzweig, N.; Rosenzweig, Z. "Superparamagnetic $Fe_2O_3$ Beads-CdSe/ZnS Quantum Dots Core-Shell Nanocomposite Particles for Cell Separation" *Nano Lett.* 2004, 4, pp. 409-413.

Huang, C.-C.; Su, C.-H.; Li, W.-M.; Liu, T.-Y.; Chen, J.-H.; Yeh, C.-S. "Bifunctional $Gd_2O_3$/C Nanoshells for MR Imaging and NIR Therapeutic Applications" *Adv. Funct. Mater.* 2009, 19, pp. 249-258.

Lauffer, R. B. "Paramagnetic Metal Complexes as Water Proton Relaxation Agents for NMR Imaging: Theory and Design" *Chem. Rev.* 1987, 87, pp. 901-927.

Bottrill, M.; Kwok, L.; Long, N. J. "Lanthanides in magnetic resonance imaging" *Chemical Society Reviews* 2006, 35, pp. 557-571.

Bae, K. H.; Kim, Y. B.; Lee, Y.; Hwang, J. Y.; Park, H.; Park, T. G. "Bioinspired Synthesis and Characterization of Gadolinium-Labeled Magnetite Nanoparticles for Dual Contrast $T_1$- and $T_2$-Weighted Magnetic Resonance Imaging" *Bioconjugate Chem.* 2010, 21, pp. 505-512.

Choi, J. S.; Lee, J. H.; Shin, T. H.; Song, H. T.; Kim, E. Y.; Cheon, J. "Self-Confirming "AND" Logic Nanoparticles for Fault-Free MRI" *J. Am. Chem. Soc.* 2010, 132, pp. 11015-11017.

Hu, F.; Jia, Q.; Li, Y.; Gao, M. "Facile synthesis of ultrasmall PEGylated iron oxide nanoparticles for dual-contrast $T_1$- and $T_2$-weighted magnetic resonance imaging" *Nanotechnology* 2011, 22, pp. 1-7.

Seo, W. S.; Lee, J. H.; Sun, X.; Suzuki, Y.; Mann, D.; Liu, Z.; Terashima, M.; Yang, P. C.; McConnell, M. V.; Nishimura, D. G.; Dai, H. "FeCo/graphitic-shell nanocrystals as advancedmagnetic-resonance-imaging and near-infrared agents" *Nat Mater* 2006, 5, pp. 971-976.

Wang, F.; Tan, W. B.; Zhang, Y.; Fan, X.; Wang, M. "Luminescent nanomaterials for biological labelling" *Nanotechnology* 2006, 17, pp. R1-R13.

Auzel, F. "Upconversion and Anti-Stokes Processes with f and d Ions in Solids" *Chem. Rev.* 2004, 104, pp. 139-173.

Gong, J.; Zhao, H.; Liu, T.; Ling, R.; Xu, J. "Value of MRCP using oral Gd-DTPA as negative contrast materials in diagnosis of atypical juxtapapillary duodenal diverticulum" *Clin. Imaging* 2009, 33, pp. 361-364.

Mai, H.-X.; Zhang, Y.-W.; Si, R.; Yan, Z.-G.; Sun, L.-d.; You, L.-P.; Yan, C.-H. "High-Quality Sodium Rare-Earth Fluoride Nanocrystals: Controlled Synthesis and Optical Properties" *J. Am. Chem. Soc.* 2006, 128, pp. 6426-6436.

Boyer, J. C.; Cuccia, L. A.; Capobianco, J. A. "Synthesis of Colloidal Upconverting $NaYF_4$: $Er^{3+}/Yb^{3+}$ and $Tm^{3+}/Yb^{3+}$ Monodisperse Nanocrystals" *Nano Lett.* 2007, 7, pp. 847-852.

Boyer, J. C.; Vetrone, F.; Cuccia, L. A.; Capobianco, J. A. "Synthesis of Colloidal Upconverting $NaYF_4$ Nanocrystals Doped with $Er^{3+}$, $Yb^{3+}$ and $Tm^{3+}$, $Yb^{3+}$ via Thermal Decomposition of Lanthanide Trifluoroacetate Precursors" *J Am. Chem. Soc.* 2006, 128, pp. 7444-7445.

Yasuo S., Y. F. "Effect of $Dy^{3+}$ on the Luminescence of $Y_3OCl_7:Yb^{3+}$. $Er^{3+}$" *Japanese Journal of Applied Physics* 1971, 10, pp. 891-901.

Wang, F.; Liu, X. "Recent advances in the chemistry of lanthanide-doped upconversion nanocrystals" *Chemical Society Reviews* 2009, 38, pp. 976-989.

Fan, H.; Leve, E. W.; Scullin, C.; Gabaldon, J.; Tallant, D.; Bunge, S.; Boyle, T.; Wilson, M. C.; Brinker, C. J. "Surfactant-Assisted Synthesis of Water-Soluble and Biocompatible Semiconductor Quantum Dot Micelles" *Nano Lett.* 2005, 5, pp. 645-648.

Viswanathan, S.; Kovacs, Z.; Green, K. N.; Ratnakar, S. J.; Sherry, A. D. "Alternatives to Gadolinium-Based Metal Chelates for Magnetic Resonance Imaging" *Chem. Rev.* 2010, 110, pp. 2960-3018.

Luce Vander Elst, A. R., Pierre Gillis, Sophie Laurent, Francois Botteman, Jeff W.M. Bulte, and Robert N. Muller "Dy-DTPA Derivatives as Relaxation Agents for Very High Field MRI: The Beneficial Effect of Slow Water Exchange on the Transverse Relaxivities" *Magn. Reson. Med.* 2002, 47, pp. 1121-1130.

Norek, M.; Kampert, E.; Zeitler, U.; Peters, J. A. "Tuning of the Size of $Dy_2O_3$ Nanoparticles for Optimal Performance as an MRI Contrast Agent" *Journal of the American Chemical Society* 2008, 130, pp. 5335-5340.

Das, G. K.; Zhang, Y.; D'Silva, L.; Padmanabhan, P.; Heng, B. C.; Chye Loo, J. S.; Selvan, S. T.; Bhakoo, K. K.; Yang Tan, T. T. "Single-Phase $Dy_2O_3:Tb^{3+}$ Nanocrystals as Dual-Modal Contrast Agent for High Field Magnetic Resonance and Optical Imaging" *Chem. Mater.* 2011, 23, pp. 2439-2446.

Norek, M.; Peters, J. A. "MRI contrast agents based on dysprosium or holmium" *Progress in Nuclear Magnetic Resonance Spectroscopy* 2011, 59, pp. 64-82.

Caravan, P. "Strategies for increasing the sensitivity of gadolinium based MRI Contrast Agents" *Chemical Society Reviews* 2006, 35, 512-523.

Caravan, P., Ellison, Jeffrey J., McMurry, Thomas J., Lauffer, Randall B. "Gadolinium(III) Chelates as MRI Contrast Agents: Structure, Dynamics, and Applications" *Chem. Rev.* 1999, 99, pp. 2293-2352.

Hyon Bin Na, J. H. L., Kwangjin An, Yong Il Park, Mihyun Park, In Su Lee, Do-Hyun Nam, Sung Tae Kim, Seung-Hoon Kim, Sang-Wook Kim, Keun-Ho Lim, Ki-Soo Kim, Sun-Ok Kim, and Taeghwan Hyeon. "Development of a T1 Contrast Agent for Magnetic Resonance Imaging Using MnO Nanoparticles" *Angew. Chem. Int. Ed.* 2007, 46, pp. 5397-5401.

Helm, L. "Optimization of gadolinium-based MRI contrast agents for high magnetic-field applications" *Future Medicinal Chemistry* 2010, 2, pp. 385-396.

Hermann, P.; Kotek, J.; Kubíček, V.; Lukeš, I. "Gadolinium(III) complexes as MRI contrast agents: ligand design and properties of the complexes" *Dalton Transactions* 2008, pp. 3027-3124.

Bridot, J.-L.; Faure, A.-C.; Laurent, S.; Rivière, C.; Billotey, C.; Hiba, B.; Janier, M.; Josserand, V.; Coll, J.-L.; Vander Elst, L.; Muller, R.; Roux, S.; Perriat, P.; Tillement, O. "Hybrid Gadolinium Oxide Nanoparticles: Multimodal Contrast Agents for in Vivo Imaging" *J. Am. Chem. Soc.* 2007, 129, pp. 5076-5084.

Das, G. K.; Heng, B. C.; Ng, S.-C.; White, T.; Loo, J. S. C.; D'Silva, L.; Padmanabhan, P.; Bhakoo, K. K.; Selvan, S. T.; Tan, T. T. Y. "Gadolinium Oxide Ultranarrow Nanorods as Multimodal Contrast Agents for Optical and Magnetic Resonance Imaging" *Langmuir* 2010, 26, pp. 8959-8965.

Evanics, F., Diamente, P. R., van Veggel, F. C. J. M., Stanisz, G. J., Prosser, R. S. "Water-Soluble $GdF_3$ and $GdF_3/LaF_3$ Nanoparticless Physical Characterization and NMR Relaxation Properties" *Chem. Mater.* 2006, 18, pp. 2499-2505.

Gossuin, Y.; Hocq, A.; Vuong, Q. L.; Disch, S.; Hermann, R. P.; Gillis, P. "Physico-chemical and NMR relaxometric characterization of gadolinium hydroxide and dysprosium oxide nanoparticles" *Nanotechnology* 2008, 19, 475102, pp. 1-8.

Jun, Y.-w.; Lee, J.-H.; Cheon, J. "Chemical Design of Nanoparticle Probes for High-Performance Magnetic Resonance Imaging" *Angew. Chem. Int. Ed.* 2008, 47, pp. 5122-5135.

(56) References Cited

OTHER PUBLICATIONS

Ralph A, H. "Multiphoton Excitation and Efficiency in the Yb3 — R.E.3~ (Ho3~,Er3~,Tm3~)Systems" *J Lumin.* 1970, 1-2, pp. 778-796.

J.C. Boyer, F. V., J.A. Capobianco, A. Speghini, M. Bettinelli "Yb3 þ ion as a sensitizer for the upconversion luminescence in nanocrystalline Gd3Ga5O12:Ho3 þ " *Chem. Phys. Lett.* 2004, 390, pp. 403-407.

Boyer, J.-C.; Gagnon, J.; Cuccia, L. A.; Capobianco, J. A. "Synthesis, Characterization, and Spectroscopy of NaGdF4: Ce3+, Tb3+/NaYF4 Core/Shell Nanoparticles" *Chem. Mater.* 2007, 19, pp. 3358-3360.

Li, Z., Zhang, Y., Jiang, S. "Multicolor Core/Shell-Structured Upconversion Fluorescent Nanoparticles" *Advanced Materials* 2008, 20, pp. 4765-4769.

Liu, B., et al. "Characterization of TectoRNA Assembly with Cationic Conjugated Polymers" *J. Am. Chem. Soc.* 2004, 126, pp. 4076-4077.

Querner, C., et al. "Carbodithioate-Containing Oligo- and Polythiophenes for Nanocrystals' Surface Functionalization" *Chem. Mater.* 2006, 18, pp. 4817-4826.

Hwang, I., et al., "Noncovalent Immobilization of Proteins on a Solid Surface by Cucurbit[7]uril-Ferrocenemethylammonium Pair, a Potential Replacement of Biotin-Avidin Pair" *J. Am. Chem. Soc.* 2007, 129, pp. 4170-4171.

X. Peng, J. Chen, J.A. Misewichb, S.S. Wong, "Carbon nanotube-nanocrystal heterostructures" *Chem. Soc. Rev.* 2009, 38, pp. 1076-1098.

H. Sami, A.K. Maparu, A. Kumar, S. Sivakumar, "Generic Delivery of Payload of Nanoparticles Intracellularly via Hybrid Polymer Capsules for Bioimaging Applications" *PLOS One* 2012, 7, 5, e36195, pp. 1-12.

L.-L. Li, R. Zhang, L. Yin, W. Qin, P.R. Selvin, Y. Lu., "Biomimetic Surface Engineering of Lanthanide-Doped Upconversion Nanoparticles as Versatile Bioprobes" *Angew Chem Int Ed Engl.* 2012, 51, 25, pp. 6121-6125.

C. Corot, P. Robert, J. M. Idée, M. Port. "Recent advances in iron oxide nanocrystal technology for medical imaging" *Adv. Drug Del. Rev.* 2006, 58, pp. 1471-1504.

ISR from PCT/SG2013/000372 dated Nov. 4, 2013.

Xia, A. et al., "Core-shell NaYF4:Yb3+, Tm3+@FexOy nanocrystals for dual-modality T2-enhanced magnetic resonance and NIR-to-NIR upconversion luminescent imaging of small-animal lymphatic node", Biomaterials, 2011, vol. 32, pp. 7200-7208.

Yang, L. W. et al., "Magnetic and upconverted luminescent properties of multifunctional lanthanide doped cubic KGdF4 nanocrystals." Nanoscale, 2010., vol. 2, pp. 2805-2810.

Guo, H., et al., "Seed-mediated synthesis of NaYF4:Yb, Er/NaGdF4 nanocrystals with improved upconversion fluorescence and MR relaxivity", Nanotechnology, 2010, vol. 21, pp. 125702-1-125602-6.

Park, Y. I., et al., "Nonblinking and nonbleaching upconverting nanoparticles as an optical imaging nanoprobe and T1 magnetic resonance imaging contrast agent", Advanced Materials, 2009, vol. 21, pp. 4467-4471.

International Preliminary Report on Patentability (Ch. II of the Patent Cooperation Treaty) dated Oct. 9, 2014.

Egeland, Ryan D. and Edwin M. Southern, Edwin. M., Electrochemically directed synthesis of oligonucleotides for DNA microarray fabrication, Nucleic Acids Research, 2005, vol. 33, No. 14, e125 doi:10.1093/nar/gni117 (7 pages).

Fortin, E., et al., "Micro-Imprinting of Oligonucleotides and Oligonucleotide Gradients on Gold Surfaces: A New Approach Based on the Combination of Scanning Electrochemical Microscopy and Surface Plasmon Resonance Imaging (SECM/ SPR-i)," Electroanalysis (2005) 17, No. 5-6, pp. 495-503.

Holt, L.J., et al., "Domain antibodies: proteins for therapy," Trends in Biotechnology, vol. 21, No. 11, Nov. 2003, pp. 484-490.

Kwon, et al., "Quantitative Evaluation of the Relative Cell Permeability of Peptoids and Peptides," J. Am. Chem. Soc. (2007), vol. 129, No. 6, pp. 1508-1509.

Mosavi, L.K., et al., "The ankyrin repeat as molecular architecture for protein recognition," Protein Science (2004) 13, 6, pp. 1435-1448.

Shumaker-Parry, J.S., et al., "Microspotting Streptavidin and Double-Stranded DNA Arrays on Gold for High-Throughput Studies of Protein-DNA Interactions by Surface Plasmon Resonance Microscopy," Analytical Chemistry, Feb. 15, 2004, vol. 76, No. 4, pp. 918-929.

Silverman, J., et al., "Multivalent avimer proteins evolved by exon shuffling of a family of human receptor domains," Nature Biotechnology, vol. 23, No. 12, Dec. 2005, pp. 1556-1561.

Skerra, A., "Engineered protein scaffolds for molecular recognition," Journal of Molecular Recognition (2000), 13, pp. 167-187.

Zhang, Y. et al., Single-Phase $NaDyF_4$:$Tb^{3+}$ Nanocrystals as Multifunctional Contrast Agents in High-Field Magnetic Resonance and Optical Imaging, Eur. J. Inorg. Chem., Apr. 2012, pp. 2044-2048.

\* cited by examiner

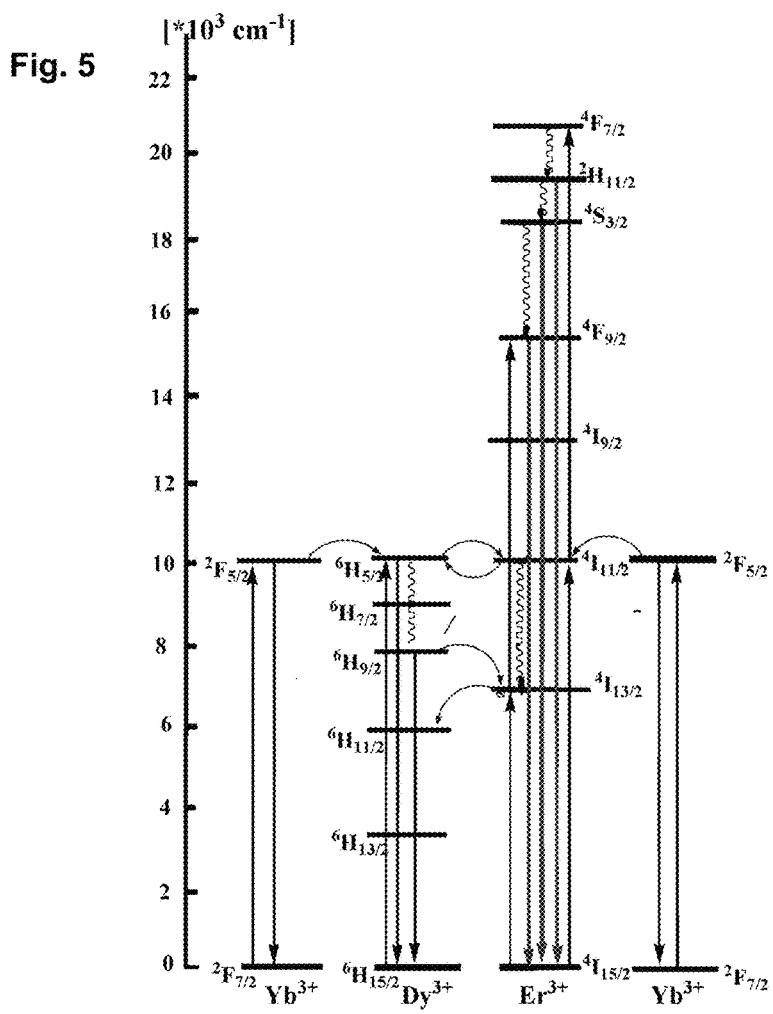
Fig. 5
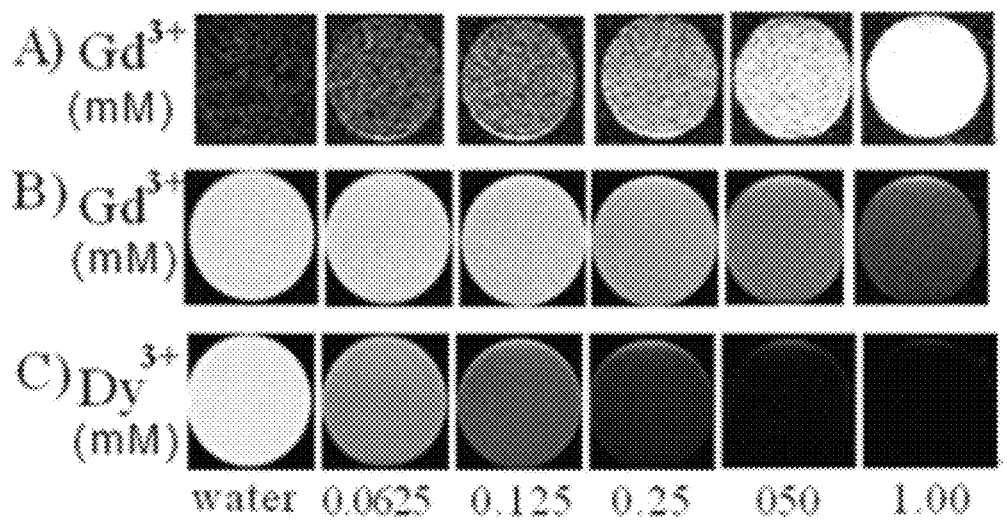
Fig. 6 (continued on next page)

NANOPARTICULATE CONTRAST AGENT

CROSS-REFERENCE TO RELATED APPLICATION

This application is the U.S. National Stage of International Patent Application No. PCT/SG2013/000372, filed on Aug. 27, 2013, which claims the benefit of and the priority to U.S. Provisional Application No. 61/693,371, entitled "A Strategy to Achieve Simultaneous Up-conversion Fluorescence and Tunable $T_1$-$T_2$ Magnetic Resonance Imaging Contrast in Lanthanide Nanocrystals", filed on Aug. 27, 2012 with the United States Patent and Trademark Office. The content of said applications are incorporated herein by reference for all purposes in their entirety including all tables, figures, and claims—as well as including an incorporation of any element or part of the description, claims or drawings not contained herein whether or not referred to in Rule 20.5(a) of the PCT, pursuant to Rule 4.18 of the PCT.

FIELD OF THE INVENTION

The present invention relates generally to a nanoparticulate contrast agent, and in particular a multimodal nanoparticulate contrast agent. Provided is inter alia a MRI contrast agent configured to manipulate both the longitudinal ($T_1$) and transverse ($T_2$) relaxation times of proton spins. In addition, the MRI contrast agent is typically configured to provide luminescence and thus an optical signal.

BACKGROUND OF THE DISCLOSURE

The following discussion of the background of the invention is merely provided to assist the reader in understanding the invention, and is not admitted to describe or constitute prior art to the present invention.

Multimodal imaging probes are highly desirable for in vivo diagnosis due to their ability to be detectable in multiple mode techniques, leading to more accurate and reliable data.[1] Multimodal probes that possess magnetic resonance (MR) as well as optical imaging capabilities have attracted considerable attention in recent years.[1a,2] Magnetic resonance imaging (MRI) offers imaging of opaque tissues in a noninvasive manner with a high spatial resolution.[3] However, its limited sensitivity for imaging at the cellular level hampers its applications for molecular imaging.[3] Optical imaging, on the other hand, provides high sensitivity for in vivo imaging, but suffers from low tissue penetration.[4] The integration of MRI and optical imaging could act synergistically by improving the resolution and sensitivity.[5] In this regard, numerous efforts have been dedicated to the fabrication of bimodal imaging contrast agents, such as Gd-Cy5.5/magnetic nanoparticles (NPs),[6] NaYF$_4$/Si-DTTA-Gd$^{3+}$ NPs,[7] Fe$_2$O$_3$/CdSe (ZnS) NPs,[8] and Gd$_2$O$_3$/C nanoshells.[9]

In particular, lanthanide nanocrystals (NCs) have been actively pursued as multimodal probes due to their unique paramagnetic and luminescent properties. Paramagnetic lanthanides, owing to their unpaired electrons, have been found to be useful as MRI contrast agents, which enhance the visualization of MRI signals. The use of MR contrast agents, which usually constitutes paramagnetic species, can enhance the contrast between normal and malignant tissues by greatly enhancing the water proton's longitudinal ($T_1$) or transverse ($T_2$) relaxation rate, the effect which is widely known as proton relaxation enhancement (PRE).[10] $T_1$ contrast agents, which typically include—paramagnetic complexes containing Gd$^{3+}$ and Mn$^{2+}$ ions, induce bright MR images in $T_1$-weighted experiments by increasing the spin-lattice relaxation rate of nearby water protons. In contrast thereto, $T_2$ contrast agents, which commonly consist of superparamagnetic NPs (e.g., iron oxide NPs) cause protons in their vicinity to undergo fast spin-spin relaxation which gives rise to dark MR images in $T_2$-weighted experiments.[11] A dual-mode imaging strategy, where $T_1$ and $T_2$ MR imaging modes can be utilized simultaneously, has the potential to obtain more comprehensive and complementary diagnostic information. For such purpose, Gd-labeled magnetite NPs[12] and "magnetically decoupled" MnFe$_2$O$_4$—Gd$_2$O(CO$_3$)$_2$ core/shell NCs were designed as dual-contrast agents for $T_1$- and $T_2$-weighted MR imaging.[13] Ultrasmall superparamagnetic iron oxide (USPIO) NPs, capable of depicting enhanced $T_1$ and weak $T_2$ contrast effects at low concentration range, have been developed.[14] A FeCo-graphitic system has also exhibited a high $T_1$ and $T_2$ contrast effect, however, an understanding of the mechanism by which this system operates is still unclear.[15]

In addition, compared to conventional imaging probes such as organic fluorescent dyes and quantum dots (QDs), lanthanides exhibit multicolor and sharp emission with high quantum yield, long luminescence lifetimes, and low toxicity.[16] These excellent features, coupled with their high resistance to photobleaching, make them highly suitable as alternatives to organic dyes and QDs for various biological applications.[16] Lanthanides also possess the ability of converting near-infrared (NIR) light (usually 980 nm) to higher energies ranging from UV to the NIR, a process known as up-conversion (UC), which is strongly desirable for biological applications as it gives rise to deeper light penetration, reduced autofluorescence and light scattering, and increasing image contrast.[17] A persisting bottleneck in achieving simultaneous UC fluorescence and dual $T_1$, $T_2$ MRI contrast in single lanthanide nanocrystals is the presence of dysprosium (Dy$^{3+}$) ions, which are up-converter quenchers. Dy$^{3+}$ ion, despite being a "poison" for UC emission, can enhance the transverse relaxation rate of water protons in tissues.[17] They are regarded as promising $T_2$ contrast agents in MRI, as they can provide better spatial resolution and higher contrast to noise ratio at higher magnetic field (>1.5 T).[11]

However, there is still a need to provide further contrast agents, in particular dual modal contrast agents.

SUMMARY OF THE INVENTION

The present disclosure can be taken to generally relate to nanoparticles as well as delivery vehicles that contain such nanoparticles. The present inventors have developed nanoparticles that are composed of matter, which allows tuning both the longitudinal ($T_1$) and transverse ($T_2$) relaxation times of proton spins such as surrounding water proton spins. In addition, the nanoparticles developed by the inventors typically have the property of upon irradiation with light they emit light at shorter wavelength than the wavelength at which they were exited. This effect is also termed "up-conversion" in the art.

The present inventors have put into practice a simple strategy to produce nanoparticles that have adjustable $T_1$ and $T_2$ relaxation times, providing a contrast in magnetic resonance techniques. The nanoparticles typically also show efficient up-conversion fluorescence. These properties can be solely based on active lanthanide elements. A nanoparticulate composite as described in this document has two or more layers. In an embodiment where the first layer contains Dysprosium and the second layer contains Erbium, "poisoning" $Dy^{3+}$ ions (supra) are being physically separated from the $Er^{3+}$ emitters. In some embodiments $Dy^{3+}$ ions are furthermore being co-doped with $Yb^{3+}$. In addition, to the ability to show strong $T_2$ contrast, by utilizing a different pulse sequence, positive or negative $T_1$ contrast can be tuned.

In a first aspect, the invention provides a nanoparticulate composite. The nanoparticulate composite contains two layers, a first and a second layer. The first layer comprises one or more metals and one or more suitable dopants. The one or more metals may be a paramagnetic metal, a ferromagnetic metal, and/or a superparamagnetic metal. The second layer contains one or more metals, which may be gadolinium such as gadolinium (III), manganese such as manganese (II), and/or iron such as iron (III). The one or more metals of the second layer are an oxide or a fluoride.

In some embodiments the nanoparticulate composite of the first aspect consists of two layers as defined above, namely the first and the second layer. In some embodiments the nanoparticulate composite of the first aspect essentially consists of the first and the second layer. In some embodiments the first layer consists of one or more metals and one or more suitable dopants. In some embodiments the first layer essentially consists of one or more metals and one or more suitable dopants. In some embodiments the second layer consists of one or more metals of gadolinium such as gadolinium (III), manganese such as manganese (II), and/or iron such as iron (III). In some embodiments the second layer essentially consists of one or more metals of gadolinium such as gadolinium (III), manganese such as manganese (II), and/or iron such as iron (III).

In some embodiments of the nanoparticulate composite of the first aspect, the first layer contains Dysprosium. In some embodiments of the nanoparticulate composite of the first aspect the first layer contains iron. In some embodiments of the nanoparticulate composite of the first aspect the one or more metals that are included in the first layer are an oxide or a fluoride. In some embodiments the one or more metals that are included in the first layer include one or more of $Dy_2O_3$, $DyF_3$, $NaDyF_4$, $LiDyF_4$, $KDyF_4$, $Fe_2O_3$, $Fe_3O_4$, $ZnFe_2O_4$, $CoFe_2O_4$, FePt, and $NiFe_2O_4$. In some embodiments the first layer includes or essentially consists of $Dy_2O_3$. In some embodiments the first layer includes or essentially consists of $DyF_3$. In some embodiments the first layer includes or essentially consists of $NaDyF_4$. In some embodiments the first layer includes or essentially consists of $LiDyF_4$. In some embodiments the first layer includes or essentially consists of $KDyF_4$. In some embodiments the first layer includes or essentially consists of $Fe_2O_3$. In some embodiments the first layer includes or essentially consists of $Fe_3O_4$. In some embodiments the first layer includes or essentially consists of $MnFe_2O_4$. In some embodiments the first layer includes or essentially consists of $ZnFe_2O_4$. In some embodiments the first layer includes or essentially consists of $CoFe_2O_4$. In some embodiments the first layer includes or essentially consists of FePt. In some embodiments the first layer includes or essentially consists of and $NiFe_2O_4$.

In some embodiments the one or more dopants that are included in the first layer of the the nanoparticulate composite of the first aspect include one or more of $Yb^{3+}$, $Fe^{3+}$, $Co^{2+}$, and $Ni^{2+}$. In one embodiment a dopant included in the first layer is $Yb^{3+}$. In one embodiment a dopant included in the first layer is $Fe^{3+}$. In one embodiment a dopant included in the first layer is $Co^{2+}$. In one embodiment a dopant included in the first layer is $Ni^{2+}$. In some embodiments the first layer contains two dopants. In one embodiment the first layer includes an $Yb^{3+}$ compound as a dopant and a $Dy^{3+}$ compound as a dopant.

In some embodiments of the nanoparticulate composite of the first aspect, the second layer contains Gadolinium. In some embodiments the second layer contains Erbium. In some embodiments the second layer contains both Gadolinium and Erbium. In some embodiments of the nanoparticulate composite of the first aspect the one or more metals included in the second layer include or essentially consist of $GdF_3$. In some embodiments the one or more metals included in the second layer include or essentially consist of $Gd_2O_3$. In some embodiments the one or more metals included in the second layer include or essentially consist of MnO. In some embodiments the one or more metals included in the second layer include or essentially consist of $Mn_3O_4$. In some embodiments the one or more metals included in the second layer include or essentially consist of $GdPO_4$. In some embodiments the one or more metals included in the second layer include or essentially consist of $LiGdF_4$. In some embodiments the one or more metals included in the second layer include or essentially consist of $NaMnF_3$. In some embodiments the one or more metals included in the second layer include or essentially consist of $KMnF_3$. In some embodiments the one or more metals included in the second layer include or essentially consist of $LiMnF_3$. In some embodiments the one or more metals included in the second layer include or essentially consist of $NaGdF_4$. In some embodiments the one or more metals included in the second layer include or essentially consist of $KGdF_4$. In some embodiments the one or more metals included in the second layer include or essentially consist of $NaY(Yb)F_4$:Gd. In some embodiments the one or more metals included in the second layer include or essentially consist of $LiY(Yb)F_4$:Gd. In some embodiments the one or more metals included in the second layer include or essentially consist of $KY(Yb)F_4$:Gd. In some embodiments the one or more metals included in the second layer include or essentially consist of $NaY(Yb)F_4$:Mn. In some embodiments the one or more metals included in the second layer include or essentially consist of $LiY(Yb)F_4$:Mn. In some embodiments the one or more metals included in the second layer include or essentially consist of $KY(Yb)F_4$:Mn. In some embodiments the one or more metals included in the second layer include or essentially consist of $LaF_3$:Gd/Mn. In some embodiments the one or more metals included in the second layer include or essentially consist of superparamagnetic iron oxide (SPIO). In some embodiments the second layer includes two or more of $GdF_3$, $Gd_2O_3$, MnO, $Mn_3O_4$, $GdPO_4$, $LiMnF_3$, $NaMnF_3$, $KMnF_3$, $LiGdF_4$, $NaGdF_4$, $KGdF_4$, $LiY(Yb)F_4$:Gd, $NaY(Yb)F_4$:Gd, $KY(Yb)F_4$:Gd, $LiY(Yb)F_4$:Mn, $NaY(Yb)F_4$:Mn, $KY(Yb)F_4$:Mn, $LaF_3$:Gd/Mn, and ultrasmall superparamagnetic iron oxide (SPIO).

In some embodiments of the nanoparticulate composite of the first aspect the second layer contains one or more lanthanide dopants. Such a lanthanide dopant is in some embodiments $Yb^{3+}$. In some embodiments the second layer contains an $Er^{3+}$ dopant. In some embodiments the second layer contains a $Tm^{3+}$ dopant. In some embodiments the second layer contains a $Ho^{3+}$ dopant. In some embodiments the second layer contains two dopants. In one embodiment the second layer includes an $Yb^{3+}$ compound as a dopant and an $Er^{3+}$ compound as a dopant. In one embodiment the second layer includes an $Yb^{3+}$ compound as a dopant and a $Tm^{3+}$ compound as a dopant. In one embodiment the second layer includes an $Yb^{3+}$ compound as a dopant and a $Ho^{3+}$ compound as a dopant. In some embodiments the second layer contains three dopants. In one embodiment the second layer includes an $Yb^{3+}$ compound as a dopant, an $Er^{3+}$ compound as a dopant and a $Tm^{3+}$ compound as a dopant. In one embodiment, the second layer includes a $Yb^{3+}$ compound as a dopant, a $Er^{3+}$ compound as a dopant and a $Ho^{3+}$ compound as a dopant. In one embodiment, the second layer includes an $Yb^{3+}$ compound as a dopant, an $Er^{3+}$ compound as a dopant and a $Tm^{3+}$ compound as a dopant. In one embodiment, the second layer includes a $Yb^{3+}$ compound as a dopant, a $Ho^{3+}$ compound as a dopant and a $Tm^{3+}$ compound as a dopant In one embodiment, the second layer includes an $Yb^{3+}$ compound as a dopant, a $Nd^{3+}$ compound as a dopant and a $Er^{3+}$ compound as a dopant. In one embodiment, the second layer includes a $Yb^{3+}$ compound as a dopant, a $Nd^{3+}$ compound as a dopant and a $Ho^{3+}$ compound as a dopant. In one embodiment, the second layer includes an $Yb^{3+}$ compound as a dopant, a $Nd^{3+}$ compound as a dopant and a $Tm^{3+}$ compound as a dopant. In one embodiment, the second layer contains four dopants. In one embodiment, the second layer includes an $Yb^{3+}$ compound as a dopant, a $Er^{3+}$ compound as a dopant, a $Ho^{3+}$ compound as a dopant and a $Tm^{3+}$ compound as a dopant. In one embodiment, the second layer includes an $Yb^{3+}$ compound as a dopant, an $Yb^{3+}$ compound as a dopant, and a $Nd^{3+}$ compound as a dopant, an $Er^{3+}$ compound as a dopant, and a $Tm^{3+}$ compound as a dopant. In one embodiment, the second layer includes an $Yb^{3+}$ compound as a dopant, a $Nd^{3+}$ compound as a dopant, a $Ho^{3+}$ compound as a dopant, and a $Tm^{3+}$ compound as a dopant. In one embodiment, the second layer includes an $Yb^{3+}$ compound as a dopant, a $Nd^{3+}$ compound as a dopant, an $Er^{3+}$ compound as a dopant, and a $Ho^{3+}$ compound as a dopant. In one embodiment, the second layer contains five dopants. In one embodiment, the second layer includes an $Yb^{3+}$ compound as a dopant, a $Nd^{3+}$ compound as a dopant, a $Er^{3+}$ compound as a dopant, a $Ho^{3+}$ compound as a dopant, and a $Tm^{3+}$ compound as a dopant.

In some embodiments the nanoparticulate composite of the first aspect is a core/shell nanocrystal. In some embodiments the nanoparticulate composite of the first aspect is a heterodimer. In some embodiments the nanoparticulate composite of the first aspect is a Janus particle. The nanoparticulate composite may for instance be a core/shell nanocrystal, in which the first layer defines the core, and the second layer defines the shell.

In some embodiments the nanoparticulate composite of the first aspect contains a surfactant immobilized on its surface. In some embodiments the surfactant is an anionic surfactant. In some embodiments the anionic surfactant is poly(acrylic) acid. In some embodiments the anionic surfactant is polyethylene glycol. In some embodiments the surfactant is a cationic surfactant. The cationic surfactant may for instance be hexadecyltrimethylammonium bromide. The cationic surfactant may also be hexadecyltrimethylammonium bromide. In some embodiments the cationic surfactant is tetramethylammonium hydroxide. In some embodiments the cationic surfactant is polyethylenimine. In some embodiments the cationic surfactant is polyvinylpyrolidone. In some embodiments the cationic surfactant is lauryl methyl gluceth-10 hydroxypropyl dimonium chloride. The cationic surfactant may also be benzethonium chloride.

In some embodiments the surfactant is a non-ionic surfactant. In some embodiments the surfactant is a zwitterionic surfactant.

In a second aspect, the invention provides a contrast agent. The contrast agent contains one or more nanoparticulate composites according to the first aspect. In some embodiments the contrast agent is a magnetic resonance imaging contrast agent. In some embodiments the contrast agent is a $T_1$-$T_2$ dual mode contrast agent. A contrast agent according to the second aspect may in some embodiments be an upconversion luminescence nanoparticulate composite, for example an upconversion fluorescence nanoparticulate composite.

In some embodiments the contrast agent according to the second aspect is configured, upon exposure to a first wavelength $\lambda_1$ of radiation, to generate a second wavelength $\lambda_2$ of radiation having a higher energy than the first wavelength $\lambda_1$. The first wavelength is generally visible or infrared light. The first wavelength is in some embodiments a wavelength in the range from about 700 nm to about 1 mm, such as from about 750 nm to about 1 mm. The first wavelength $\lambda_1$ can be about 800 nm. The first wavelength $\lambda_1$ can be 915 nm. The first wavelength $\lambda_1$ can be 980 nm. In such embodiments the contrast agent exhibits a radiation, e.g. light, emission upon interaction with a wavelength $\lambda_1$. This light emission is of a wavelength $\lambda_2$. The emission wavelength can be from UV to NIR range. In some embodiments the emission wavelength is in the range from about 3 $\lambda$m to about 10 nm. The wavelength $\lambda_2$ is higher than the wavelength $\lambda_1$. Accordingly, the emitted radiation, e.g. light, has a higher wavelength, and therefore higher energy, than the absorbed radiation.

In a third aspect, the invention relates to the use of a nanoparticulate composite according to the first aspect in performing magnetic resonance imaging.

DESCRIPTION OF THE DRAWINGS

FIG. 5 illustrates the proposed energy transfer processes responsible for the UC emission of $NaGdF_4$:$Yb^{3+}$, $Er^{3+}$; triple dopant $NaGdF_4$:$Yb^{3+}$, $Er^{3+}$, $Dy^{3+}$; $NaDyF_4$:$Yb^{3+}$/$NaGdF_4$:$Yb^{3+}$, $Er^{3+}$, $Yb^{3+}$-absent $NaDyF_4$/$NaGdF_4$:$Yb^{3+}$, $Er^{3+}$ NCs and $NaDyF_4$:$Yb^{3+}$, $Er^{3+}$/$NaGdF_4$. Vertical and wavy arrows represent non-radiative transitions, curved arrows represent non-radiative energy transfer, green and red arrows represent green and red emissions.

DETAILED DESCRIPTION

Figure 1:
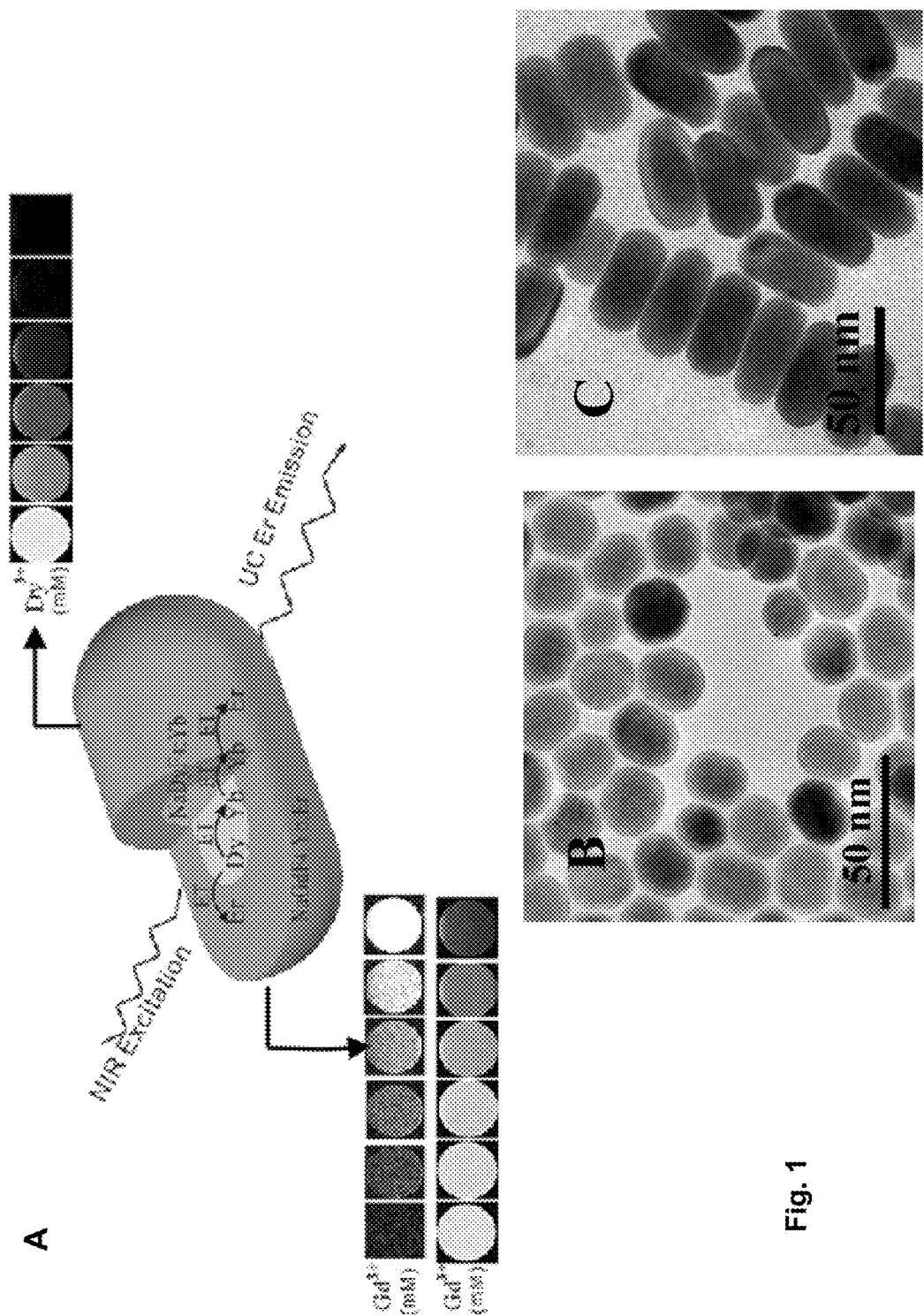
FIG. 1: (A) is a schematic illustration of the general strategy to achieve tunable MRI $T_1$-$T_2$ contrast and up-conversion lanthanide nanocrystals (NCs). (B) and (C) show TEM images of the seed $NaDyF_4$:$Yb^{3+}$ NCs (B) and $NaDyF_4$:$Yb^{3+}$/$NaGdF_4$:$Yb^{3+}$, $Er^{3+}$ NCs (C).

Provided herein is inter alia a nanoparticle as well as a plurality of nanoparticles. The present inventors could show that nanoparticles as described in this document can be used as a contrast agent in vivo, acting both as a negative and a positive contrast agent. The contrast agent can be adjusted according to the diagnostic set-up and tissue concerned.

The word "about" as used herein refers to a value being within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. The term "about" is also used to indicate that the amount or value in question may be the value designated or some other value that is approximately the same. The phrase is intended to convey that similar values promote equivalent results or effects according to the invention. In this context "about" may refer to a range above and/or below of up to 10%. The word "about" refers in some embodiments to a range above and below a certain value that is up to 5%, such as up to up to 2%, up to 1%, or up to 0.5% above or below that value. In one embodiment "about" refers to a range up to 0.1% above and below a given value.

The term "administering", as used herein, refers to any mode of transferring, delivering, introducing, or transporting matter such as a compound, e.g. a pharmaceutical compound, or other agent such as an antigen, to a subject. Modes of administration include oral administration, topical contact, intravenous, intraperitoneal, intramuscular, intranasal, or subcutaneous administration (cf. below). Administration "in combination with" further matter such as one or more therapeutic agents includes simultaneous (concurrent) and consecutive administration in any order.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

The term "antibody" generally refers to an immunoglobulin, a fragment thereof or a proteinaceous binding molecule with immunoglobulin-like functions (cf. below).

The word "assay" as used in this document refers to a method, generally known in the art, to analyse a feature, e.g. a catalytic activity, the presence, the formation or the amount of matter occurring in a biological specimen. Such matter may be occurring in a living organism or representing a living organism, such as a protein, a nucleic acid, a lipid, a cell, a virus, a saccharide, a polysaccharide, a vitamin or an ion, to name a few examples. The word "assay" emphasizes that a certain procedure or series of procedures is followed, which may be taken to represent the respective assay. An assay may include quantitated reagents and established protocols to assess the presence, absence, amount or activity of a biological entity.

The term "binding partner" as used herein refers to matter, such as a molecule, in particular a polymeric molecule, that can bind a nucleic acid molecule such as a DNA or an RNA molecule, including an mRNA molecule, as well as a peptide, a protein, a saccharide, a polysaccharide or a lipid through an interaction that is sufficient to permit the agent to form a complex with the nucleic acid molecule, peptide, protein or saccharide, a polysaccharide or a lipid, generally via non-covalent bonding. In some embodiments the binding partner is a PNA molecule. In some embodiments the binding partner is an immunoglobulin or a proteinaceous binding molecule with immunoglobulin-like functions as defined below. In some embodiments the binding partner is an aptamer. In some embodiments a binding partner is specific for a particular target. In some embodiments a binding partner includes a plurality of binding sites, each binding site being specific for a particular target. As an illustrative example, a binding partner may be a proteinaceous agent with immunoglobulin-like functions with two binding sites. It may for instance be a bispecific diabody, such as a bispecific single chain diabody.

The term "essentially consists of" is understood to allow the presence of additional components in a sample or a composition that do not affect the properties of the sample or a composition. As an illustrative example, a pharmaceutical composition may include excipients if it essentially consists of an active ingredient.

The term "layer" as used herein refers to a defined space occupied by particular matter. Typically a layer is a particular portion of an object. A layer may for example occupy a space that is unevenly distributed in the three dimensions of space. In this regard the term layer may be a definition relative to another portion of an object. Thus a layer may be a portion of an object that spreads along another portion of an object, for example below or above the other portion of the object. In some embodiments a layer has a defined thickness. In some embodiments a layer has an at least essentially uniform thickness.

The term "nucleic acid molecule" as used herein refers to any nucleic acid in any possible configuration, such as single stranded, double stranded or a combination thereof. Examples of nucleic acids include for instance DNA molecules, RNA molecules, analogues of the DNA or RNA generated using nucleotide analogues or using nucleic acid chemistry, locked nucleic acid molecules (LNA), protein nucleic acids molecules (PNA), alkylphosphonate and alkylphosphotriester nucleic acid molecules and tecto-RNA molecules[37]. LNA has a modified RNA backbone with a methylene bridge between C4' and O2', providing the respective molecule with a higher duplex stability and nuclease resistance. Alkylphosphonate and alkylphosphotriester nucleic acid molecules can be viewed as a DNA or an RNA molecule, in which phosphate groups of the nucleic acid backbone are neutralized by exchanging the P—OH groups of the phosphate groups in the nucleic acid backbone to an alkyl and to an alkoxy group, respectively. DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label.

Many nucleotide analogues are known and can be used for the nanoparticulate composits and in the methods disclosed in this specification. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. Modifications at the base moiety may be a natural or a synthetic modification of A, C, G, and T/U, a different purine or pyrimidine base, such as uracil-5-yl, hypoxanthin-9-yl, and 2-aminoadenin-9-yl, as well as a non-purine or a non-pyrimidine nucleotide base. Other nucleotide analogues serve as universal bases. Examples of universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

The term "subject" as used herein, also addressed as an individual, refers to a human or non-human animal, generally a mammal. A subject may be of a mammalian species such as a rabbit, a mouse, a rat, a Guinea pig, a hamster, a dog, a cat, a pig, a cow, a goat, a sheep, a horse, a monkey, an ape or a human. Thus, the methods, uses and compositions described in this document are applicable to both human and veterinary disease. As explained in more detail below, the sample has been obtained from the subject. It is thus understood that conclusions drawn from expression levels in the sample and decisions based thereon concern the subject from whom/which the sample has been taken. Further, while a subject is typically a living organism, a method or use described in this document may also be used in post-mortem analysis. Where the subject is a living human who is receiving medical care for a disease or condition, it is also addressed as a "patient".

The terms "comprising", "including, containing", "having" etc. shall be read expansively or open-ended and without limitation. Thus the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the word "having". When used herein "consisting of" excludes any element, step, or ingredient not specified in the defined element, e.g. claim element. When used herein, "consisting essentially of" does not exclude materials or steps that do not materially affect the basic and novel characteristics of the respective definition or claim.

Singular forms such as "a", "an" or "the" include plural references unless the context clearly indicates otherwise. Thus, for example, reference to a "compound" includes a single compound as well as a plurality of compounds, either the same or different. Likewise reference to a "nanocrystal" includes a single nanocrystal as well as a plurality of nanocrystals. Unless otherwise indicated, the term "at least" preceding a series of elements is to be understood to refer to every element in the series. The terms "at least one" and "at least one of" include for example, one, two, three, four, or five or more elements. It is furthermore understood that slight variations above and below a stated range can be used to achieve substantially the same results as a value within the range. Also, unless indicated otherwise, the disclosure of ranges is intended as a continuous range including every value between the minimum and maximum values.

The scope and meaning of any use of a term will be apparent from the specific context in which the term is used. Certain further definitions for selected terms used throughout this document are given in the appropriate context of the detailed description, as applicable. Unless otherwise defined, all other scientific and technical terms used in the description, figures and claims have their ordinary meaning as commonly understood by one of ordinary skill in the art.

A nanoparticulate composite as disclosed herein may be any nanoparticle. Examples of a suitable nanoparticle include, but are not limited to, a nanocrystal, a nanosphere, a nanorod, a nanotube, a nanowire, a nanocup, and a nanodumbbel. A respective particle may be several hundred nanometers in size or smaller. A nanoparticle is a particle that has a maximal width in at least one dimension that is 100 nm or less. In some embodiments the particle has a maximal size (i.e. in the dimension of its maximal width, e.g. diameter) of about 0.1 to about 1000 nanometers, such as about 1 to about 1000 nm, about 5-900 nm, about 2-200 nm or about 10-600 nm or about 20-500 nm. In some embodiments a plurality of particles, e.g. nanoparticles, is used. In some of such embodiments all particles may be of identical geometry, while in other embodiments nanoparticles of different geometry are used. A nanoparticulate composite as disclosed herein is in some embodiments electrically conductive and has in some embodiments magnetic properties.

A nanoparticulate composite as disclosed herein is generally a solid particle. It may have a dimension across its length of below about 1 μm, such as below about 200 nm, or below about 50 nm. As noted above, a respective magnetic nanoparticle may for instance include superparamagnetic matter (e.g. $Fe_3O_4$ or $\gamma$-$Fe_2O_3$), such as a core of such matter.

The nanoparticulate composite includes, in some embodiments consists of, a first and a second layer. The first and a second layer may be arranged in any position relative to each other. In one embodiment the second layer defines a circumferential portion of the nanoparticulate composite, for example a covering or shroud, surrounding the first layer. In one embodiment the first layer defines a circumferential portion of the nanoparticulate composite, surrounding the second layer.

The first layer contains a paramagnetic metal, a ferromagnetic metal, and/or a superparamagnetic metal. A ferromagnetic metal is strongly attracted by a magnet. It can also be used to form a permanent magnet. Ferromagnetism it is the type of magnetism that creates forces strong enough to be felt, and is responsible for the common phenomena of magnetism encountered in everyday life. A few illustrative examples of a ferromagnetic metal are iron, in particular in the form of $Fe_3O_4$, Dysprosium, Gadolinium, Nickel, or Cobalt. A paramagnetic metal has unpaired electrons and is also attracted by a magnet, however to a lesser extent. In addition to this weak, positive magnetic susceptibility a paramagnetic metal is not able to remain magnetic in the absence of an applied magnetic field. A large variety of paramagnetic metals are known, in particular many transition metals are known to be paramagnetic. A few illustrative examples of paramagnetic metal ions are $Ba^{2+}$, $Ce^{3+}$, $Nd^{3+}$, $Sm^{3+}$, $Tb^{3+}$, $Ho^{3+}$, $Er^{3+}$, $Tm^{3+}$ $Mn^{2+}$, $Eu^{3+}$, $Gd^{3+}$ and $Dy^{3+}$. Paramagnetic materials have been used as MRI contrast agents because of their long recognized ability to decrease $T_1$ (see below). Paramagnetic MRI contrast agents are usually transition metal ions of manganese or gadolinium.

A superparamagnetic metal is a ferromagnetic metal that can be magnetized by a magnet by a much larger amount if provided in the form of nanoparticles when compared to micro or macro size. Hence, a superparamagnetic material is also not able to remain magnetic in the absence of an applied magnetic field. A superparamagnetic material can have magnetic susceptibilities nearly as high as a ferromagnetic material and far higher than paramagnetic materials. When used as an MRI contrast agent, superparamagnetic and ferromagnetic materials alter the MR image by decreasing $T_2$ resulting in image darkening (see below).

In some embodiments the first layer contains dysprosium. In some embodiments the first layer contains dysprosium and lithium. In some embodiments the first layer contains dysprosium and sodium. In some embodiments the first layer contains dysprosium and potassium. In some embodiments the first layer contains $DyF_3$. In some embodiments the first layer contains iron, for example an iron oxide. In some embodiments the first layer contains both zinc and iron. In some embodiments the first layer contains both copper and iron. In some embodiments the first layer contains europium. In some embodiment the first layer contains both europium and dysprosium. In some embodiment the first layer contains both europium and iron. In some embodiments the first layer contains cobalt. In some embodiments the first layer contains both iron and cobalt. In some embodiments the first layer contains nickel. In some embodiments the first layer contains both iron and nickel.

The second layer may contain an oxide, or a phosphate, or a fluoride of gadolinium. In some embodiments the second layer may also contain manganese (II). In some embodiments the second layer may contain an oxide of manganese (II). In some embodiments the second layer may contain lithium (I) and manganese (II). In some embodiments the second layer may contain sodium and manganese (II). In some embodiments the second layer may contain potassium and manganese (II).

In some embodiments the second layer may contain lithium and gadolinium. In some embodiments the second layer may contain sodium and gadolinium. In some embodiments the second layer may contain potassium and gadolinium. In some embodiments the second layer may contain ultrasmall superparamagnetic iron oxide nanoparticles. Typically such ultrasmall superparamagnetic iron oxide nanoparticles have a maximal width of about 5 nm or less.

Medical imaging modalities allow the visualization of the organs within a mammal, such as a human body. Magnetic resonance imaging (MRI) has become a popular technique for noninvasive imaging of opaque specimens due to its high spatial and temporal resolution. MRI uses a powerful magnetic field to align the nuclear magnetization of protons in water. MRI can produce images with large contrast to render detailed images of the body in any plane. MRI generally provides much greater contrast between different soft tissues of the body as compared to other techniques, making it particularly useful in musculoskeletal imaging, cardiovascular and vascular imaging, neurological imaging, oncological imaging and other body parts or functions and diseases. Unlike CT or PET, MRI uses no ionizing radiation, but instead uses a magnetic field to align the nuclear magnetization of atoms (usually hydrogen atoms) in the body. The MRI imaging techniques therefore provide high quality images without exposing the patient to any kind of harmful radiation.

In MRI an image of an organ or tissue is obtained by placing a subject in a strong magnetic field and observing the interactions between the magnetic spins of the protons and radiofrequency electromagnetic radiation. The magnetic spins produce an oscillating magnetic field which induces a small current in the receiver coil, wherein this signal is called the free induction decay (FID). Two parameters, termed proton relaxation times, are of primary importance in the generation of the image. They are called $T_1$, also called the spin-lattice or longitudinal relaxation time, and $T_2$, the spin-spin or transverse relaxation time. Spin relaxation is a term used in the art to characterize the return of the transverse magnetization, the xy component of the net magnetization vector at right angles to the main magnetic field, to its equilibrium value, zero. The parameter $T_1$ refers to the amount of time it takes for tissue magnetization to return to its equilibrium state in the longitudinal direction of the main magnetic field after excitation with a radiofrequency pulse. The excess energy that is absorbed by the magnetic spins from a radiofrequency pulse is transferred back to the ambience during the relaxation process. The parameter $T_2$ can be understood to refer to a transfer of excess energy between magnetic spins, after such energy has been deposited in the tissue by a radiofrequency pulse. This transferred energy results in loss of spin phase coherency in the transverse plane and spin dephasing.

Owing to their different $T_1$ and $T_2$ relaxation, tissues may be distinguished. Image contrast is created by differences in the strength of the MRI signal recovered from different locations within the tissue or sample. This depends upon the relative density of excited nuclei (such as water protons), on differences in the relaxation times of those nuclei. The type of imaging pulse sequence may also affect contrast. MRI provides good soft tissue contrast on unenhanced images. However, in some situations, the contrast generated may not adequately show the tissues, anatomy or pathology as desired, and a contrast agent may enhance such contrast. As an illustrative example, many brain metastases can only be visualized after contrast enhancement A contrast agent alters relaxation times ($T_1$ and $T_2$) of protons within a sample and enhances contrast in the image, thereby enhancing the diagnostic power of MRI. A contrast agent is a compound that exerts an effect on the nuclear magnetic resonance (NMR) parameters of various chemical species around them. Contrast agents for MRI that are available may be injected intravenously to enhance the appearance of tumors, blood vessels and/or inflammation for example. Contrast agents may also be directly injected into a joint, for MR images of joints, referred to as arthrograms. Contrast agents may also be taken orally for some imaging techniques. Since MRI images can be generated from an analysis of the $T_1$ and $T_2$ parameters, it is desirable to have a contrast agent which affects both parameters.

Currently available contrast agents are usually classified according to their effect on either $T_1$ or $T_2$. Positive contrast agents cause a reduction in the $T_1$ relaxation time. Such a contrast agent generally contains as its active element Gadolinium, or Manganese. All of these elements have unpaired electron spins in their outer shells and long relaxivities. Negative contrast agents generate predominantly spin spin relaxation effects, thought to reflect local field inhomogeneities, which results in shorter $T_1$ and $T_2$ relaxation times. A negative contrast agent appears predominantly dark on MRI, while a positive contrast agent appears generally bright on MRI. This is due to the fact that reducing $T_1$ results in increased signal intensity on a $T_1$-weighted image, whereas reducing $T_2$ results in decreased signal intensity on a $T_2$-weighted image.

In a nanoparticle as described herein generally the first layer can be taken to define a $T_2$ contrast agent, and the second layer can be taken to define a $T_1$ contrast agent. A nanoparticle as described herein generally has the advantage of showing tunable properties of positive $T_1$ and negative $T_1$ by applying appropriate pulse sequences, as well as negative $T_2$ MRI contrast. In addition to possessing the advantages of normal positive $T_1$ contrast agents for clear visualization of anatomic details and bright contrast for distinguishing from other pathogenic or biological condition, the current NCs also possess the advantages of negative $T_1$ contrast agents. One of the disadvantages of using positive $T_1$ contrast agent is the bright signal they generate which causes artifacts in the bowel lumen.[18] This may be avoided if the signal can be tuned to a dark contrast.

Generally a $T_2$ weighted measurement consumes more experimental time, due to large repetition time (TR) and echo time (TE), when compared to a $T_1$ weighted measurement. Since a nanoparticulate composite as disclosed herein generates negative $T_1$ enhancement (small TR and TE), it can find application in cases where negative contrast is desired within a limited experimental time. Therefore, depending on the tissue site of interest, a nanoparticulate composite as disclosed herein can be selectively tuned to visualize by bright or dark $T_1$ and $T_2$-weighted MRI contrast in order to achieve complementary information that cannot be obtained by using single mode contrast agents. In addition, using a nanoparticulate composite as disclosed herein, the image quality can also be improved, leading to more accurate diagnosis.

The relaxivities of a nanoparticulate composite disclosed herein may be optimized by varying the concentration of any dopant used. The relaxivities of the nanoparticulate composite may also be optimized by providing an additional layer, arranged between the first and the second layer, for instance sandwiched between the first and the second layer. Such an additional layer may be configured to be inert with regard to luminescence. Such an additional layer may in some embodiments be void of Er. In some embodiments such an additional layer may be void of Ho. In some embodiments such an additional layer may be void of Tm. In some embodiments a respective additional layer may be void of Er, Ho, and Tm. In some embodiments such an additional layer may contain Gd or Mn ions. In some embodiments such an additional layer contains $NaGdF_4$. In some embodiments such an additional layer contains $GdF_3$. In some embodiments such an additional layer contains $Mn_3O_4$. In some embodiments a respective additional layer contains MnO. In some embodiments such an additional layer contains or $SiO_2$. In embodiments where the first and the second layer define an inner and an outer layer of a nanoparticle, such an additional layer may define an intermediate layer, for example a circumferential layer surrounding the inner layer such as the first layer. As an illustrative example, where the first layer contains Dysprosium ions in the form of $Dy^{3+}$ and the second layer contains Gadolinium ions in the form of $Gd^{3+}$, a physical barrier may separate these two metals and thereby reduce the effect of Dysprosium on Gadolinium.

Upconversion luminescence is a nonlinear anti-Stokes' emission process, which re-emits a photon at a shorter wavelength by absorbing more than one photon successively at longer wavelengths via longlived intermediate energy states of upconversion luminescence matter. Typically two low-energy photons are converted into a single photon at a higher energy. Upconversion luminescence matter such as a typical nanoparticulate composite described herein can be excited by low power continuous wave lasers, and even by non-coherent light sources, thus allowing its use in inter alia medical and life science applications, but also for example photovoltaic light harvesting. As an illustrative example, long wavelength near-infrared (around 980 nm) irradiation can be converted into shorter wavelength visible light emission.

Because upconversion stimulates or produces emission at shorter wavelengths, there are applications directed to medicine where the longer wavelength light is more capable than a shorter wavelength light of penetrating deep into biological tissue. Accordingly, with typical nanoparticulate matter according to this disclosure, which defines an upconverter material, pre-positioned inside for example a biological tissue or an aqueous solution, light of a longer wavelength (such as from a commercial IR laser) can be used in one embodiment to image deep skin tissue (with the upconverter material emitting visible or NIR light for detection), and/or the longer wavelength light in one embodiment can be used to excite the upconverters in the biological tissue and thereafter produce shorter wavelength light (e.g., ultraviolet light) to drive photochemical or pharmaceutical reactions in the body.

As explained above, nanoparticulate matter according to this disclosure typically shows up-conversion luminescence. In some embodiments the up-conversion emission can be used as the triggering source for drug release or other forms of therapy, while the tunable MRI contrasts can be used for diagnostics or tracking, thus fulfilling the requirement of theranostic nanomaterials, i.e. materials for diagnostic and therapeutic applications, integrating imaging and therapy.

When using a typical nanoparticulate composite as described herein, the simultaneous up-conversion luminescence and tunable $T_1$-$T_2$ contrast enhancement in MRI may be used to generate both a tunable positive and negative $T_1$ contrast effect as well as a negative $T_2$ signal—and thus observe signal complementarily. As a result, more accurate diagnosis through reduction of misdiagnosis is possible when compared to conventional techniques. Furthermore, $T_1$ and $T_2$ MR imaging can be simultaneously obtained by simple operation within the same MR imaging device, thus allowing diagnosis time and diagnosis cost to be remarkably reduced. In addition, a nanoparticulate composite as disclosed herein, providing a $T_1$-$T_2$ dual-modal contrast agent, may be applied to photodynamic therapy, hyperthermia and drug delivery systems.

Nanoparticulate matter according to this disclosure can be produced using any desired method. In some embodiments the nanoparticulate matter has a core-shell structure and may be termed a core/shell nanoparticle. Such a particle may be figured as containing two layers or shells, the inner layer, or core being one of the first and the second layer as defined above. The other, outer layer or shell being the other of the first and the second layer as defined above. A core/shell nanoparticle has a quantum dot core, that is a core defined by a nanocrystal containing or consisting of semiconductor material. The formation of nano crystals is well known in the art. As an example, a wet chemical method such as chemical precipitation, sol-gel, microemulsion, thermal decomposition or inverse micelle formation may be used. A wet chemical method typically involves a three-component system composed of a precursor, an organic surfactant, and a solvent, which is being heated. Colloidal methods, molecular beam epitaxy, metallorganic vapor phase epitaxy, lithography, milling or etching are illustrative examples of known techniques. A respective shell of nanoparticulate matter may also be formed by doping.

In some embodiments the nanoparticulate matter is a hybrid nanocrystal with a spatial anisotropic distribution of components contained therein. A hybrid nanocrystal can be taken to consist of two or more nanocrystals or nanorods connected epitaxially. A hybrid nanocrystal can be formed via any desired method. A typical method is based on a seed-growth mechanism and may include a one-pot synthesis of both components or a stepwise synthesis with premade seed particles. A hybrid nanocrystal can also be obtained by thermal annealing of nanoparticles and/or nanospheres.

In some embodiments the nanoparticulate matter is obtained by grafting matter onto a nanoparticle. As an example, a magnetic entity may be grafted on a fluorescent nanocrystal. In some embodiments epitaxial overcoating is used to provide an outer layer, for instance an outer layer defined by the first layer (supra) on an inner layer defined by the second layer, or an outer layer defined by the second layer (supra) on an inner layer defined by the first layer.

A nanoparticulate composite as described herein may have been exposed to organic surface passivation or inorganic surface passivation. In some embodiments a capping ligand may be used, for example a coordinating solvent such as trioctylphosphine oxide, oleic acid, or oleylamine.

Where desired molecules may be chemically bound to the nanoparticulate composite, e.g. to a nanocrystal. The relatively large surface to volume ratio of the nanoparticulate composite can be used to adjust the solubility or to prevent or achieve certain desired/undesired interactions with matter of the ambience. The surface may for instance modified to render the nanoparticulate composite polar, such as hydrophilic. Various organic and inorganic molecules have also been used in the art to modify the optical properties of nanocrystals and can likewise be used on nanoparticulate matter disclosed herein. In some embodiments the surface of the nanoparticulate composite may be coated with an amphiphilic polymer. Nanocrystal embedded polymer matrices, such as a polymer/quantum dots nanocomposite, polymer/quantum dots hybrid material, are well known in the art. As an example, the formation of polyallylamine capsules and the subsequent formation of nanoparticles therein has been described by Sami.[41] The loaded polymer capsules are reported to have been taken up by HeLa cells. As a further example, the surface of a nanoparticle may be coated with a monolayer of phospholipids as described by Li et al.[42]

To this extent, functional groups may be formed on an accessible surface area of the particle. The linking molecule ethylenediamine may for instance be immobilised on a respective nanoparticle. As a further illustrative example, an ionisable thiol compound such as 2-dimethyl-aminoethanethiol hydrochloride may be covalently linked to the surface of the particle. As a further example, thiophenedithiobenzoic acid may be grafted onto a metal surface, such as a nano crystal. A coordinating solvent may be employed for such purposes. If desired, a surface functionalized with thiophenedithiobenzoic may further be provided with oligo- and polythiophenes containing a carbodithioate group[38] before immobilising matter thereon.

A suitable functional group may in some embodiments directly linked to the matter forming the particle, such as a metal. In some embodiments the functional group may be included in a chemical moiety on the surface of the substrate. In some embodiments the functional group may be introduced and thus formed on the surface by means of a chemical reaction. For this purpose bifunctional compounds may for instance be used, some of which are also known as cross-linking agents. Such bifunctional compounds include two reactive centers that can each independently undergo a reaction under chosen reaction conditions. Where desired, one of the functional groups may be masked so as to remain unchanged during a first reaction, for example a covalent coupling to the surface. Any suitable bifunctional compound may be used that results in the formation of a selected functional group on the surface. The two functional groups of a respective bifunctional compound may be different or identical. They may include any functional group for a coupling to the surface familiar to those skilled in the art. Examples include, but are not limited to, organometal- (such as organomagnesiumchloride-, e.g. the well known Grignard-reagents, organomercury-, organozincchloride-, organolithium- or organopotassium-groups), organoboron- (e.g. organoboronic acids, organoboronate esters, or organoboranes), chloride, fluoride, bromide, iodide, cyano-, thiocyano-, trifluoromethyl sulfonyl-, p-toluenesulfonyl-, bromobenzenesulfonyl-, nitrobenzenesulfonyl-, methanesulfonyl-, azido-, amino-, amido-, carboxyl- (including anhydrides), hydroxyl-, thio-, and seleno-groups. Examples of compounds with two identical functional groups include, but are not limited to, diols, dicarboxylic acids, dicarboxylic acid anhydrides, diamides, dialdehydes (also as protected by dithioacetals), diamines, dithiols, difunctional dithianes, diselenols, difunctional organoboronic acids or dimetallic compounds.

In some embodiments nanoparticulate matter as described herein is coupled to a molecule with binding affinity for a selected target molecule, such as a microorganism, a virus particle, a peptoid, a protein, a nucleic acid, a peptide, an oligosaccharide, a polysaccharide, an inorganic molecule, a synthetic polymer, a small organic molecule or a drug.

A peptide may be of synthetic origin or isolated from a natural source by methods well-known in the art. The natural source may be mammalian, such as human, blood, semen, or tissue. A peptide, including a polypeptide may for instance be synthesized using an automated polypeptide synthesizer. Illustrative examples of polypeptides are an antibody, a fragment thereof and a proteinaceous binding molecule with antibody-like functions. Examples of (recombinant) antibody fragments are Fab fragments, Fv fragments, single-chain Fv fragments (scFv), diabodies or domain antibodies (Holt, L. J., et al., *Trends Biotechnol.* (2003), 21, 11, 484-490). An example of a proteinaceous binding molecule with antibody-like functions is a mutein based on a polypeptide of the lipocalin family (WO 03/029462, Beste et al., *Proc. Natl. Acad. Sci. U.S.A.* (1999) 96, 1898-1903). Lipocalins, such as the bilin binding protein, the human neutrophil gelatinase-associated lipocalin, human Apolipoprotein D or glycodelin, posses natural ligand-binding sites that can be modified so that they bind to selected small protein regions known as haptens. Examples of other proteinaceous binding molecules are the so-called glubodies (see e.g. internation patent application WO 96/23879), proteins based on the ankyrin scaffold (Mosavi, L. K., et al., *Protein Science* (2004) 13, 6, 1435-1448) or crystalline scaffold (e.g. internation patent application WO 01/04144) the proteins described in Skerra, *J. Mol. Recognit.* (2000) 13, 167-187, and avimers. Avimers contain so called A-domains that occur as strings of multiple domains in several cell surface receptors (Silverman, J., et al., Nature Biotechnology (2005) 23, 1556-1561). Peptoids, which can act as protein ligands, are oligo(N-alkyl) glycines that differ from peptides in that the side chain is connected to the amide nitrogen rather than the a carbon atom. Peptoids are typically resistant to proteases and other modifying enzymes and can have a much higher cell permeability than peptides (see e.g. Kwon, Y. U., and Kodadek, T., *J. Am. Chem. Soc.* (2007) 129, 1508-1509).

As a further illustrative example, a linking moiety such as an affinity tag may be used to immobilise the respective molecule. Such a linking moiety may be a molecule, e.g. a hydrocarbon-based (including polymeric) molecule that includes nitrogen-, phosphorus-, sulphur-, carben-, halogen- or pseudohalogen groups, or a portion thereof. As an illustrative example, the selected surface may include, for instance be coated with, a brush-like polymer, for example with short side chains. The immobilisation surface may also include a polymer that includes a brush-like structure, for example by way of grafting. It may for example include functional groups that allow for the covalent attachment of a biomolecule, for example a molecule such as a protein, a nucleic acid molecule, a polysaccharide or any combination thereof. Examples of a respective functional group include, but are not limited to, an amino group, an aldehyde group, a thiol group, a carboxy group, an ester, an anhydride, a sulphonate, a sulphonate ester, an imido ester, a silyl halide, an epoxide, an aziridine, a phosphoramidite and a diazoalkane.

Examples of an affinity tag include, but are not limited to biotin, dinitrophenol or digoxigenin, oligohistidine, polyhistidine, an immunoglobulin domain, maltose-binding protein, glutathione-S-transferase (GST), calmodulin binding peptide (CBP), FLAG'-peptide, the T7 epitope (Ala-Ser-Met-Thr-Gly-Gly-Gln-Gln-Met-Gly), maltose binding protein (MBP), the HSV epitope of the sequence Gln-Pro-Glu-Leu-Ala-Pro-Glu-Asp-Pro-Glu-Asp of herpes simplex virus glycoprotein D, the hemagglutinin (HA) epitope of the sequence Tyr-Pro-Tyr-Asp-Val-Pro-Asp-Tyr-Ala, the "myc" epitope of the transcription factor c-myc of the sequence Glu-Gln-Lys-Leu-Ile-Ser-Glu-Glu-Asp-Leu, or an oligonucleotide tag. Such an oligonucleotide tag may for instance be used to hybridise to an immobilised oligonucleotide with a complementary sequence. A further example of a linking moiety is an antibody, a fragment thereof or a proteinaceous binding molecule with antibody-like functions.

A further example of linking moiety is a cucurbituril or a moiety capable of forming a complex with a cucurbituril. A cucurbituril is a macrocyclic compound that includes glycoluril units, typically self-assembled from an acidcatalyzed condensation reaction of glycoluril and formaldehyde. A cucurbit[n]uril, (CB [n]), that includes n glycoluril units, typically has two portals with polar ureido carbonyl groups. Via these ureido carbonyl groups cucurbiturils can bind ions and molecules of interest. As an illustrative example cucurbit[7]uril (CB[7]) can form a strong complex with ferrocenemethylammonium or adamantylammonium ions. Either the cucurbit[7]uril or e.g. ferrocenemethylammonium may be attached to a biomolecule, while the remaining binding partner (e.g. ferrocenemethylammonium or cucurbit[7]uril respectively) can be bound to a selected surface. Contacting the biomolecule with the surface will then lead to an immobilisation of the biomolecule. Functionalised CB[7] units bound to a gold surface via alkanethiolates have for instance been shown to cause an immobilisation of a protein carrying a ferrocenemethylammonium unit.[39]

Further examples of a linking moiety include, but are not limited to an oligosaccharide, an oligopeptide, biotin, dinitrophenol, digoxigenin and a metal chelator (cf. also below). As an illustrative example, a respective metal chelator, such as ethylenediamine, ethylenediaminetetraacetic acid (EDTA), ethylene glycol tetraacetic acid (EGTA), diethylenetri-aminepentaacetic acid (DTPA), N,N-bis(carboxymethyl)glycine (also called nitrilotriacetic acid, NTA), 1,2-bis (o-aminophenoxy)ethane-N,N,N',N'-tetraacetic acid (BAPTA), 2,3-dimercapto-1-propanol (dimercaprol), porphine or heme may be used in cases where the target molecule is a metal ion. As an example, EDTA forms a complex with most monovalent, divalent, trivalent and tetravalent metal ions, such as e.g. silver ($Ag^+$), calcium ($Ca^{2+}$), manganese ($Mn^{2+}$), copper ($Cu^{2+}$), iron ($Fe^{2+}$), cobalt ($Co^{3+}$) and zirconium ($Zr^{4+}$), while BAPTA is specific for $Ca^{2+}$. In some embodiments a respective metal chelator in a complex with a respective metal ion or metal ions defines the linking moiety. Such a complex is for example a receptor molecule for a peptide of a defined sequence, which may also be included in a protein. As an illustrative example, a standard method used in the art is the formation of a complex between an oligohistidine tag and copper ($Cu^{2+}$), nickel ($Ni^{2+}$), cobalt ($Co^{2+}$), or zink ($Zn^{2+}$) ions, which are presented by means of the chelator nitrilotriacetic acid (NTA).

Avidin or streptavidin may for instance be employed to immobilise a biotinylated nucleic acid, or a biotin containing monolayer of gold may be employed (Shumaker-Parry, J. S., et al., *Anal. Chem.* (2004) 76, 918). As yet another illustrative example, the biomolecule may be locally deposited, e.g. by scanning electrochemical microscopy, for instance via pyrrole-oligonucleotide patterns (e.g. Fortin, E., et al., *Electroanalysis* (2005) 17, 495). In other embodiments, in particular where the biomolecule is a nucleic acid, the biomolecule may be directly synthesised on the surface of the immobilisation unit, for example using photoactivation and deactivation. As an illustrative example, the synthesis of nucleic acids or oligonucleotides on selected surface areas (so called "solid phase" synthesis) may be carried out using electrochemical reactions using electrodes. An electrochemical deblocking step as described by Egeland & Southern (*Nucleic Acids Research* (2005) 33, 14, e125) may for instance be employed for this purpose. A suitable electrochemical synthesis has also been disclosed in US patent application US 2006/0275927. In some embodiments lightdirected synthesis of a biomolecule, in particular of a nucleic acid molecule, including UV-linking or light dependent 5'-deprotection, may be carried out.

The molecule that has a binding affinity for a selected target molecule may be immobilised on the nanoparticulate composite by any means. As an illustrative example, an oligo- or polypeptide, including a respective moiety, may be covalently linked to the surface of the nanoparticulate composite via a thio-ether-bond, for example by using w functionalized thiols. Any suitable molecule that is capable of linking nanoparticulate matter to a molecule having a selected binding affinity may be used to immobilise the same on a nanoparticulate composite as described herein. For instance a (bifunctional) linking agent such as ethyl-3-dimethylaminocarbodiimide, N-(3-aminopropyl) 3-mercapto-benzamide, 3-aminopropyl-trimethoxysilane, 3-mercaptopropyl-trimethoxysilane, 3-(trimethoxysilyl) propylmaleimide, or 3-(trimethoxysilyl) propyl-hydrazide may be used. Prior to reaction with the linking agent, the surface of the nanoparticulate composite can be modified, for example by treatment with glacial mercaptoacetic acid, in order to generate free mercaptoacetic groups which can then employed for covalently coupling with an analyte binding partner via linking agents.

In some embodiments a nanoparticulate composite described herein may be included in a liposome, i.e. in an artificially-prepared vesicle defined by a circumferential lipid layer, typically a lipid bilayer. A respective liposome is typically defined by one or more lipids, and may in some embodiments largely or essentially contain phospholipids that form bilayers similar to those found in biomembranes. Nanocrystal encapsulated liposomes are well known in the art and also referred to as "nanovials".

A nanoparticulate composite may also be included in a dendrimer, i.e. a molecule that is repetitively branched. A dendrimer is generally monodisperse and typically highly symmetric and spherical. A dendrimer may be a hyper-branched polymer, a polymer brush. Typically three major portions can be distinguished in a dendrimer, namely a core, an inner shell, and an outer shell. In some embodiments the core is defined by a nanoparticulate composite as described above. In some embodiments a dendrimer is formed by immobilizing a compound on a nanoparticulate composite, for instance a compound with one or more tertiary amino groups, which can be used as a monomer for synthesizing a dendrimer. Subsequently a dendrimer may be produced on the nanoparticulate composite. In some embodiments a dendrimer is water soluble, a property that may be achieved via functionalizing the outer shell of any dendrimer with charged moieties and/or polar groups.

In some embodiments a nanoparticulate composite as described herein is encompassed, including encapsulated by a perfluorocarbon such as a perfluoroalkane. A respective perfluoroalkane may in some embodiments be a compound that is per se a gas such as tetrafluoromethane, hexafluoroethane or octafluorocyclobutan. In some embodiments a nanoparticulate composite as described herein is encompassed, including encapsulated by a fluoroalkylsilane. Illustrative examples of a fluoroalkylsilane are triethoxy(heptafluoropropyl)-silane (Chemical Abstracts No. 874906-86-2), tributoxy(2,2-difluoroethyl)silane (Chemical Abstracts No. 4168-06-3), (2,2-difluoroethyl)trimethoxysilane (CAS No. 994-46-7), trimeth-oxy(1,1,2,2-tetrafluoroethyl)silane (CAS No. 356-49-0), trimethoxy(nonafluorobutyl)-silane (CAS No. 84464-03-9), trimethoxy(undecafluoropentyl)silane (CAS No. 84464-04-0), trimeth-oxy(pentadecafluoroheptyl)silane (CAS No. 84464-06-2), trimethoxy(tridecafluorohexyl)silane (CAS No. 84464-05-1), (heptadecafluorooctyl)trimethoxysilane (CAS No. 88101-77-3), (heptafluoropropyl)trimethoxysilane (CAS No. 129051-17-8), 3,3,7,7-tetramethoxy-4-[1,2,2,2-tetra-fluoro-1-(heptafluoropropoxy)ethyl]-6-[2,3,3,3-tetrafluoro-2-(heptafluoropropoxy) propyl]-2,8-dioxa-3,7-disilanonane (CAS No. 135179-25-8), trimethoxy(pentatriacontafluoro-heptadecyl)-silane (CAS No. 864979-41-9), 7-[2-(2-aminoethoxy)ethoxy]-7-(3,3,4,4,5,5,6,6,7,7,8,8,8-tri-decafluorooctyl)-3,6,8,11-tetraoxa-7-silatridecane-1,13-diamine (CAS No. 887651-71-0), diethoxy(trifluoromethyl)methyl-silane (CAS No. 167408-24-4), dimethoxybis(trifluoromethyl)-silane (CAS No. 173162-24-8), diethoxy[2,2,2-trifluoro-1,1-bis(trifluoromethypethyl](trifluoro-ethenyl)silane (CAS No. 841313-62-0), dimethoxymethyl(2,2,2-trifluoro-l-methylethyl)silane (CAS No. 84442-94-4), (1,3,3,4,4, 5,5,6,6,7,7,8,8,9,9,9-hexadecafluorononyl)dimethoxymethyl-silane (CAS No. 879495-27-9), methoxydimethyl (pentadecafluoroheptyl)silane (CAS No. 855774-07-1), and ethoxydimethyl(trifluorovinyl)silane (CAS No. 5674-84-0).

In some embodiments a nanoparticulate composite as described herein is encompassed, including encapsulated by a silicon alkoxide such as methyl silicate (Si(OMe)$_4$), ethyl silicate (Si(OEt)$_4$), propyl silicate (Si(OPr)$_4$), isopropyl silicate (Si(Oi—Pr)$_4$), pentyl silicate (Si(OCH$_5$H$_{11}$)$_4$), octyl silicate (Si(OC$_8$H$_{17}$)$_4$), isobutyl silicate (Si(OCH$_2$iPr)$_4$), tetra(2-ethylhexyl) orthosilicate (Si(OCH$_2$C(Et)n-Bu)$_4$), tetra(2-ethylbutyl) silicate (Si(OCH$_2$CHEt$_2$)$_4$), ethylene silicate ((C$_2$H$_4$O$_2$)$_2$Si), tetrakis(2,2,2-trifluoroethoxy)silane (Si (OCH$_2$CF$_3$)$_4$), tetrakis(methoxyethoxy)silane (Si (OCH$_2$CH$_2$OMe)$_4$), benzyl silicate or cyclopentyl silicate.

In some embodiments a nanoparticulate composite as described herein is encompassed in a nanotube such as a carbon nanotube. A respective nanotube may include any material or composite of materials allowing electrical conductivity, such as a metal (e.g. a gold or a silver nanowire), a semiconductor (e.g. a silicon or a gallium nitride nanowire) or a polymer. Carbon nanotubes can be either metallic or semiconducting. Metallic nanocrystals have been for instance been found to be able to enter a carbon nanotube, if a current is applied to the tube, and even pass through portions of a carbon nanotube with a smaller width than the width of the nanocrystal. As a further example, composites of carbon nanotubes and nanocrystals have been produced with multi-walled carbon nanotubes via electrophoretic deposition. Besides a direct formation of nanoparticles on carbon nanotubes, nanotube-nanoparticle heterostructures may be prepared via covalent coupling or non-covalent coupling such as by electrostatic interactions, hydrophobic interactions or π-π stacking interaction. An overview on producing carbon nanotube-nanoparticle heterostructures has been given by Peng et al.[40] Furthermore, numerous approaches have been presented to functionalize or chemically alter carbon nanotubes in order to provide them with a chemical reactivity or to increase their solubility in certain liquids. Illustrative examples include hydrogenation, halogenation, ozonolysis, plasma activation, addition of moieties including grafting or cycloadditions.

A contrast agent as described herein can be used in the generating an image of a human or non-human subject, which generally involves administering the contrast agent to the subject (e.g. vascularly, via the gastrointestinal tract, etc.) and generating an image of at least a part of the subject to which the contrast agent has distributed.

A contrast agent as described herein may be administered to a subject via any known method for administering therapeutics and diagnostics. For example, fluids that include pharmaceutically and physiologically acceptable fluids, including water, physiological saline, balanced salt solutions, buffers, aqueous dextrose, glycerol or the like as a vehicle, can be administered by any method used by those skilled in the art. These solutions are typically sterile and generally free of undesirable matter. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration and imaging modality selected. Provided are further formulations that include the contrast agent and a pharmaceutically acceptable excipient Generally the formulation is suitable for administration as an imaging enhancing agent and the contrast agent is present in an amount sufficient to enhance a magnetic resonance tomography image. These agents can be administered by any means in any appropriate formulation. Detergents can also be used to stabilize the composition or the increase or decrease the absorption of the composition. Other physiologically acceptable compounds include wetting agents, emulsifying agents, dispersing agents or preservatives that are particularly useful for preventing the growth or action of microorganisms. One skilled in the art would appreciate that the choice of an acceptable carrier, including a physiologically acceptable compound depends, e.g. on the route of administration and on the particular physio-chemical characteristics of any co-administered agent.

Methods of introduction include, but are not limited to, intradermal, intramuscular, intraperitoneal, intravenous, subcutaneous, intranasal, rectal, vaginal, and oral routes. The compositions may be administered by any convenient route, for example by infusion or bolus injection, by absorption through epithelial or mucocutaneous linings (e.g., oral mucosa, vaginal, rectal and intestinal mucosa, etc.) and may be administered together with other biologically active agents. Administration can be systemic or local. In addition, the contrast agent(s) compositions may be introduced into the central nervous system by any suitable route, including intraventricular and intrathecal injection; intraventricular injection may be facilitated by an intraventricular catheter, for example, attached to a reservoir, such as an Ommaya reservoir. The contrast agent can be delivered by any means known in the art systematically (e.g. intravenously), regionally or locally (e.g. intra- or peri-tumoral or intra-cystic injection, e.g. to image bladder cancer) by e.g. intra-arterial, intra-tumoral, intra-venous (iv), parenteral, intra-pneural cavity, topical, oral or local administration, as sub-cutaneous intra-zacheral (e.g. by aerosol) or transmucosal (e.g. voccal, bladder, vaginal, uterine, rectal, nasal, mucosal), intra-tumoral (e.g. transdermal application or local injection). For example, intra-arterial injections can be used to have a "regional effect", e.g. to focus on a specific organ (e.g. brain, liver, spleen, lungs). For example intra-hepatic artery injection or intra-carotid artery injection may be used. If it is decided to deliver the preparation to the brain, it can be injected into a carotid artery or an artery of the carotid system of arteries (e.g. ocipital artery, auricular artery, temporal artery, cerebral artery, maxillary artery etc.).

In some embodiments, amounts of the contrast agents sufficient to provide the desired results will be used, balanced by other considerations such as whether the contrast agent used for a particular application might produce undesirable physiological results. In some embodiments, the precise dose to be employed in the formulation can also depend on the route of administration, and should be decided according to the judgment of the practitioner and each subject's circumstances. In addition, in vitro and in vivo assays may optionally be employed to help identify optimal dosage ranges. Effective doses may be extrapolated from dose-response curves derived from in vitro or in vivo test systems. In some embodiments, the amounts of the contrast agent or agents administered can range from micromolar to molar amounts, but more likely will be used in millimolar-to-micromolar amounts.

A formulation containing the contrast agent can be administered in a variety of unit dosage forms, depending upon the particular cell or tissue or cancer to be imaged, the general medical condition of each patient, the method of administration, and the like. Details on dosages are well described on the scientific and patent literature. The exact amount and concentration of contrast agent and the amount of formulation in a given dose, or the "effective dose" can be routinely determined by, e.g. the clinician. The "dosing regimen" will depend upon a variety of factors, e.g. whether the cell or tissue or tumor to be imaged is disseminated or local, the general state of the patient's health, and age. Using guidelines describing alternative dosing regimens, e.g. from the use of other imaging contrast agents, the skilled artisan can determine by routine trials optimal effective concentrations of a formulation containing the contrast agent.

The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are set forth within the following claims. In addition, where features or aspects of the invention are described in terms of Markush groups, those skilled in the art will recognize that the invention is also thereby described in terms of any individual member or subgroup of members of the Markush group.

In order that the invention may be readily understood and put into practical effect, particular embodiments will now be described by way of the following non-limiting examples.

Examples

The following examples are solely provided in order to demonstrate and further illustrate certain embodiments and aspects of the present invention and are by no means to be construed as limiting the scope thereof.

A schematic illustration of the general strategy to achieve tunable MRI $T_1$-$T_2$ contrast and up-conversion lanthanide nanocrystals can be taken from FIG. 1A. The TEM images of seed $NaDyF_4$:$Yb^{3+}$ NCs and $NaDyF_4$:$Yb^{3+}$/$NaGdF_4$:$Yb^{3+}$, $Er^{3+}$ NCs are shown in FIGS. 1B, 1C. The image of the seed NCs (FIG. 1B) displayed signs of anisotropic growth. The nanorods (NRs) in the presence of $Gd^{3+}$ and $Er^{3+}$ showed relatively uniform rod-shape morphology, due to the well defined orientation and growth (FIG. 1C). The average diameter and length of the $NaDyF_4$:$Yb^{3+}$ NCs are 17 and 22 nm, respectively. The average diameter and length of the $NaDyF_4$:$Yb^{3+}$/$NaGdF_4$:$Yb^{3+}$, $Er^{3+}$ NRs are 21 and 45 nm, respectively.

Figure 2:
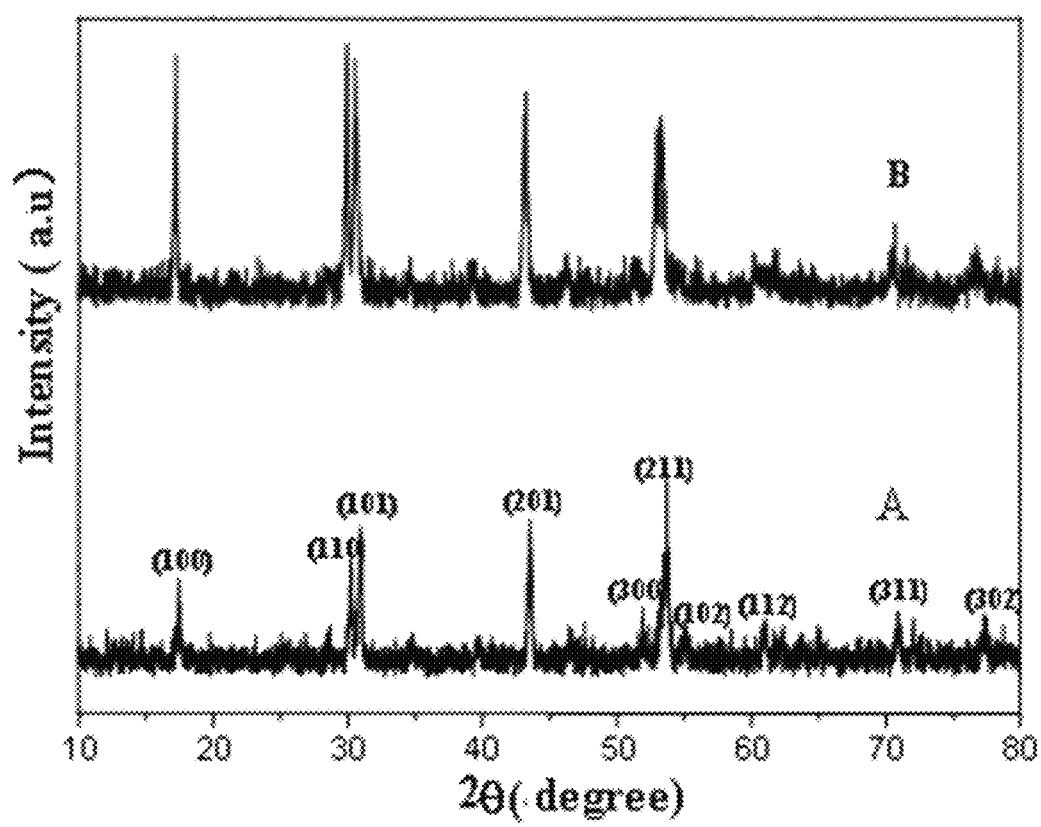
FIG. 2 shows XRD patterns of as-synthesized $NaDyF_4$:$Yb^{3+}$ NCs (A) and $NaDyF_4$:$Yb^{3+}$/$NaGdF_4$:$Yb^{3+}$, $Er^{3+}$ nanorods (NRs) (B).
Figure 3:
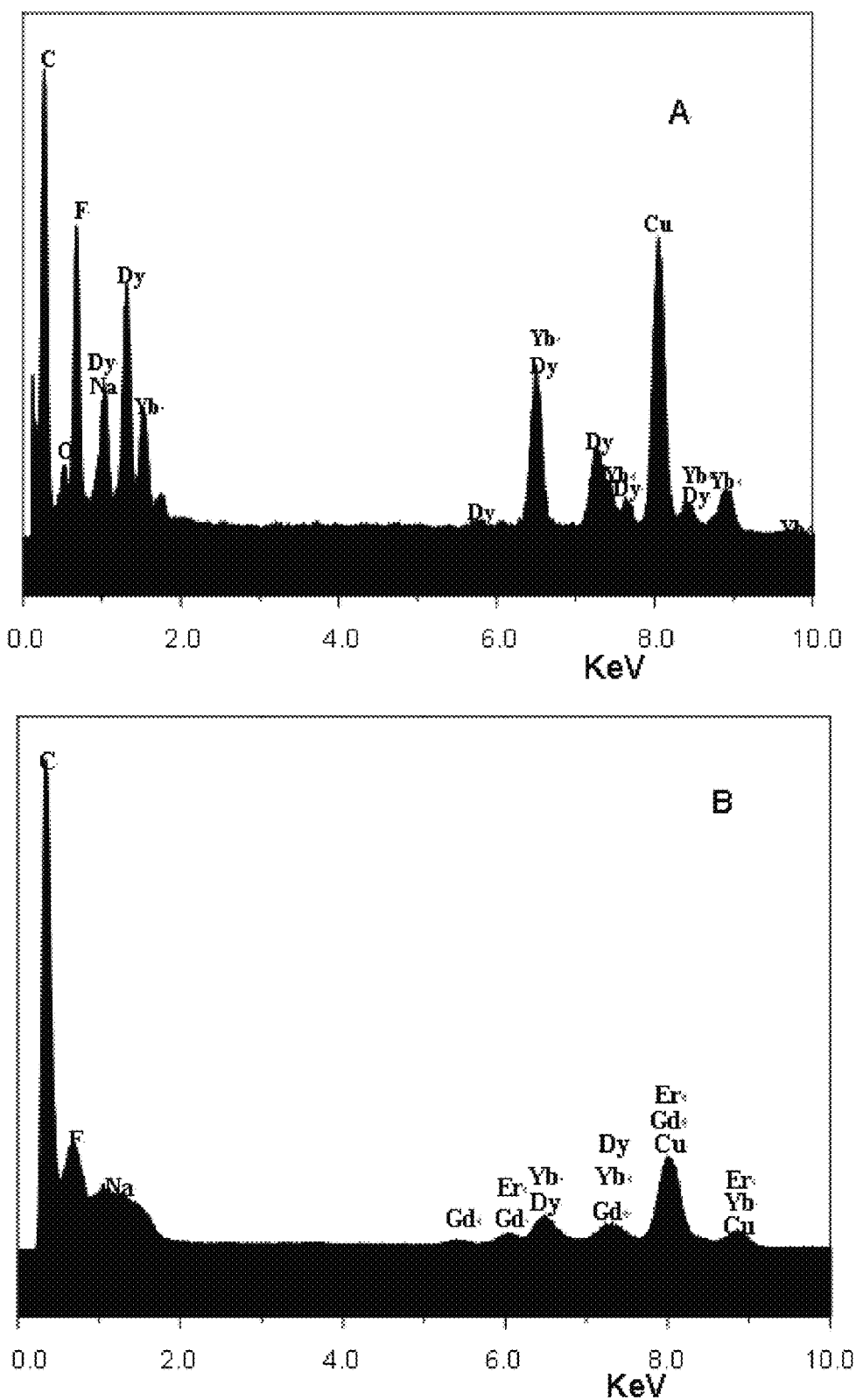
FIG. 3 depicts energy-dispersive X-ray spectroscopy (EDX) analysis of (A) $NaDyF_4$:$Yb^{3+}$ and (B) $NaDyF_4$:$Yb^{3+}$/$NaGdF_4$:$Yb^{3+}$, $Er^{3+}$ NCs, revealing the presence of the Gd, Er after secondary growth on the $NaDyF_4$:$Yb^{3+}$ seeds NCs.

The hexagonal phase structure of the $NaDyF_4$:$Yb^{3+}$ NCs and $NaDyF_4$:$Yb^{3+}$/$NaGdF_4$:$Yb^{3+}$, $Er^{3+}$ NRs were confirmed by the XRD analysis (FIG. 2). The peak positions and intensities of the seed NCs are consistent with hexagonal-phase $NaDyF_4$.[19] The XRD pattern of the $NaDyF_4$:$Yb^{3+}$/$NaGdF_4$:$Yb^{3+}$, $Er^{3+}$ NRs is similar to that of the seed NCs, but with an increase in peak signal intensity. The increased intensity is attributed to the increase in size of the NCs and similar crystal structure of $NaDyF_4$ and $NaGdF_4$. Energy-dispersive X-ray analysis (EDX) confirmed the presence of all elements in the seed NCs (Na, Dy, F, Yb) and NRs (Gd, Er in addition to all seed elements) (see FIG. 3). Using inductively coupled plasma mass spectroscopy (ICP-MS), the Gd:Dy molar ratio was quantified to be 40.2:40, based on the stoichiometric ratio of the chloride precursors used in the experiment.

Figure 4A:
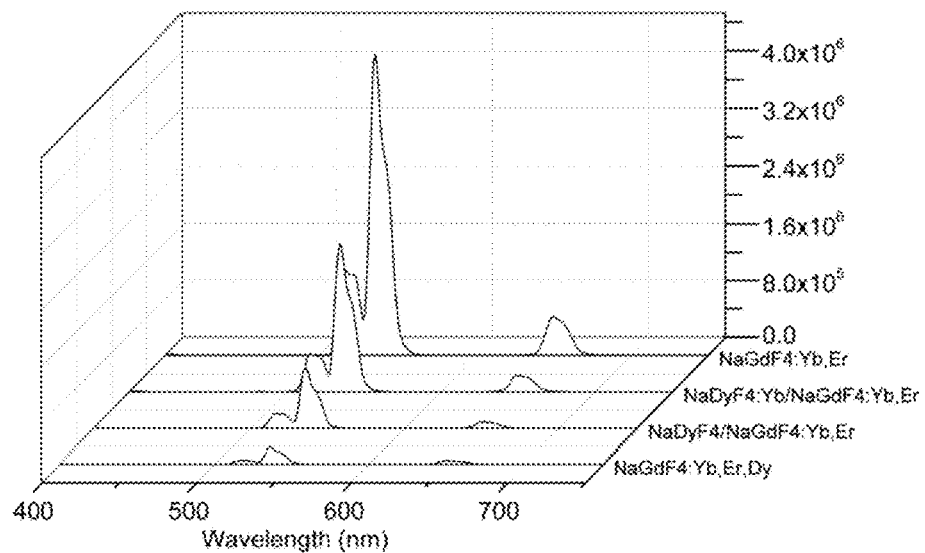
FIG. 4A shows UC fluorescence spectra of (I) $NaGdF_4$:$Yb^{3+}$,$Er^{3+}$, (ii) $NaDyF_4$:$Yb^{3+}$/$NaGdF_4$:$Yb^{3+}$, $Er^{3+}$, (iii) $Yb^{3+}$-absent $NaDyF_4$/$NaGdF_4$:$Yb^{3+}$, $Er^{3+}$; (iv) triple dopant $NaGdF_4$:$Yb^{3+}$, $Er^{3+}$, $Dy^{3+}$ and $NaDyF_4$:$Yb^{3+}$, $Er^{3+}$/$NaGdF_4$ (v) NCs at the excitation of 980 nm (1 wt %).
Figure 4B:
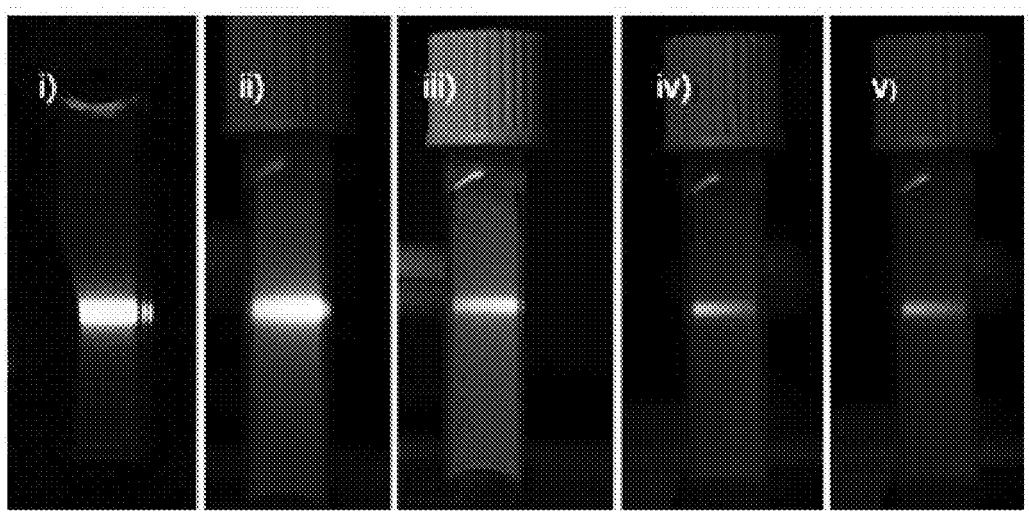
FIG. 4B shows photographs of green emissions of water-soluble (i) $NaGdF_4$:$Yb^{3+}$, $Er^{3+}$, (ii) $NaDyF_4$:$Yb^{3+}$/$NaGdF_4$:$Yb^{3+}$, $Er^{3+}$, (iii) $Yb^{3+}$-absent $NaDyF_4$/$NaGdF_4$:$Yb^{3+}$, $Er^{3+}$, (iv) triple doped $NaGdF_4$:$Yb^{3+}$, $Er^{3+}$, $Dy^{3+}$ and $NaDyF_4$:$Yb^{3+}$, $Er^{3+}$/$NaGdF_4$ (v) NCs (1 wt %). Samples concentration was 1 mg/ml and spectra were recorded at a power of 1 W.

To demonstrate the feasibility of this strategy, the inventors synthesized five types of NCs. FIG. 4A shows the UC emission spectra of (i) $NaGdF_4$:$Yb^{3+}$, $Er^{3+}$; (ii) $NaDyF_4$:$Yb^{3+}$/$NaGdF_4$:$Yb^{3+}$, $Er^{3+}$; (iii) $Yb^{3+}$-absent $NaDyF_4$/$NaGdF_4$:$Yb^{3+}$, $Er^{3+}$; (iv) triple-doped $NaGdF_4$:$Yb^{3+}$, $Er^{3+}$, $Dy^{3+}$ and (v) $NaDyF_4$:$Yb^{3+}$, $Er^{3+}$/$NaGdF_4$ NCs, excited at 980 nm. All the NCs exhibited green and red emissions. There are no characteristic emission lines of $Dy^{3+}$ ions in the wavelength regions of 470-500 nm and 570-600 nm, indicating that $Yb^{3+}$ ions act as the main sensitizer and $Er^{3+}$ ions the emitters. Therefore, green emissions at 523 and 546 nm are ascribed to $Er^{3+}$ ions transition from $^2H_{11/2}$ and $^4S_{3/2}$ excited states to the $^4I_{15/2}$ ground state respectively, while red emission at 659 nm is due to the transition from $^4F_{9/2}$ excited state to the ground state of $Er^{3+}$ ions.[20] The intensities of green emission of all NCs are much stronger in comparison with those of red emissions, as shown in FIG. 4B.

The intensities of the green emissions of NCs (ii)-(v) are weaker than that of (i) $NaGdF_4$:$Yb^{3+}$, $Er^{3+}$ NCs, due to the detrimental effect of $Dy^{3+}$ ions (FIG. 5). $Dy^{3+}$ ions are well-known UC quenchers. One explanation for $Dy^{3+}$ ions quenching of $Er^{3+}$ luminescence is the depopulation of $^4I_{11/2}$ ($Er^{3+}$) and $^2F_{5/2}$ ($Yb^{3+}$) by $Dy^{3+}$ ions. Because the $^2F_{5/2}$-$^2F_{7/2}$ transition of $Yb^{3+}$ ions and $^4I_{11/2}$-$^4I_{15/2}$ transition of $Er^{3+}$ ions are resonant with the $^6H_{5/2}$-$^6H_{5/2}$ transition of $Dy^{3+}$ ions, energy transfer between $Yb^{3+}$, $Er^{3+}$ and $Dy^{3+}$ can take place. $Dy^{3+}$ ions can receive energy from the excited $Yb^{3+}$ and $Er^{3+}$ ions, or excited by 980 nm photon, populating the $^6H_{5/2}$ excited state from $^6H_{15/2}$ ground state. The life time of $^6H_{5/2}$ is short, and so back-energy transfer to $Yb^{3+}$ ions is negligible.[21] The excited $Dy^{3+}$ ions can either relax radiatively to ground state, or relax non-radiatively to the $^6H_{9/2}$ level of which the transition energy is transferred to the $Er^{3+}$ ions for excitation from the ground level ($^4I_{15/2}$) to the first excitation level ($^4I_{13/2}$). The second and third energy transfers from the $Dy^{3+}$ ions to $Er^{3+}$ at the $^4I_{13/2}$ can cause $Er^{3+}$ excitation from the first excitation level ($^4I_{13/2}$) to a higher $^4F_{9/2}$ level and subsequently to the upper excitation level ($^2H_{9/2}$). A radiative transition from $^2H_{9/2}$ to $^4I_{11/2}$ level ensues and gives rise to red emission around 660 nm. This three-photon excitation process has been demonstrated by a study of up-conversion $Er^{3+}$ emissions in the presence of $Dy^{3+}$ ions.[21] However, the efficiency of this three-photon excitation efficiency is low compared to the $Yb^{3+}$—$Er^{3+}$ energy transition process. As sensitizers, $Yb^{3+}$ ions have only one excitation level at 980 nm and exhibit a much larger absorption cross-section at this level, working more efficiently as sensitizing centers in comparison with $Dy^{3+}$ ions.

$NaDyF_4$:$Yb^{3+}$/$NaGdF_4$:$Yb^{3+}$, $Er^{3+}$ (ii) and $NaDyF_4$/$NaGdF_4$:$Yb^{3+}$, $Er^{3+}$ (iii) NCs show stronger emission than triple doped $NaGdF_4$:$Yb^{3+}$, $Er^{3+}$, $Dy^{3+}$ (iv) and $NaDyF_4$:$Yb^{3+}$, $Er^{3+}$/$NaGdF_4$ (v) (FIG. 4(a)), highlighting the advantages of the current NCs with varying composition to circumvent the detrimental effect of $Dy^{3+}$ ions. The emitters $Er^{3+}$ ions are physically separated from the $Dy^{3+}$ ions, minimizing the energy transfers to $Dy^{3+}$ ions which led to quenching of $Er^{3+}$ luminescence. By comparing the $NaDyF_4$:$Yb^{3+}$/$NaGdF_4$:$Yb^{3+}$ $Er^{3+}$ and $NaDyF_4$/$NaGdF_4$:$Yb^{3+}$, $Er^{3+}$ NCs, it was observed that the up-conversion emission intensity was further enhanced upon doping the core with $Yb^{3+}$ ions. Dopant concentration determines the distance between two neighboring ions and has a great impact on the efficiency of energy transfer and hence the up-conversion efficiency of lanthanide ions doped NCs.[22] Increasing $Yb^{3+}$ ions population in the core "tricks" the $Dy^{3+}$ ions to undergo energy transfer with the "sacrificial" $Yb^{3+}$ ions, reducing the quenching effect on the $Er^{3+}$ ions. The increase in $Yb^{3+}$ sensitization centers also facilitates greater population of $Er^{3+}$ ions to the $^4F_{7/2}$ state via two successive energy transfers ($^4I_{15/2}$-$^4I_{11/2}$, $^4I_{11/2}$-$^4I_{7/2}$), of which $Er^{3+}$ ions decay to give rise to green ($^2H_{11/2}$-$^4I_{15/2}$, $^4S_{3/2}$-$^4I_{15/2}$) and red ($^4F_{9/2}$-$^4I_{15/2}$) emissions (FIG. 5). It should be noted that the presence of $Gd^{3+}$ ions should not affect the above-discussed energy transfer due to the large energy gap (32,000 cm$^{-1}$) between the ground $^8S_{7/2}$ and first excited states $^6P_{7/2}$.

Figure 6D:
In FIG. 6D to FIG. 6F (i) represents a control, 0.8% agarose, and (ii) represents NC fixed in 0.8% agarose.
Figure 6E:
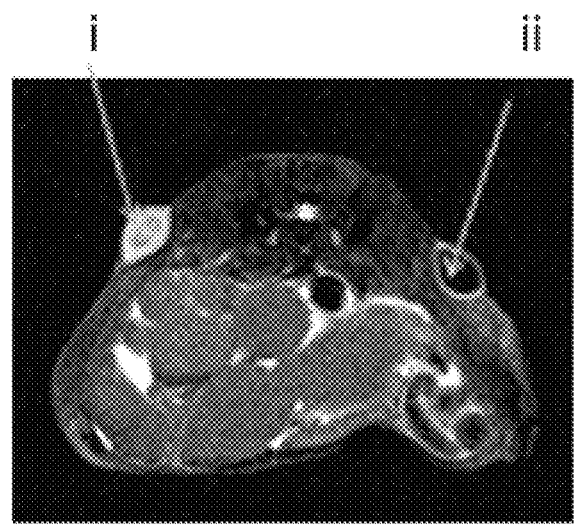
Figure 6F:
Figure 6G:
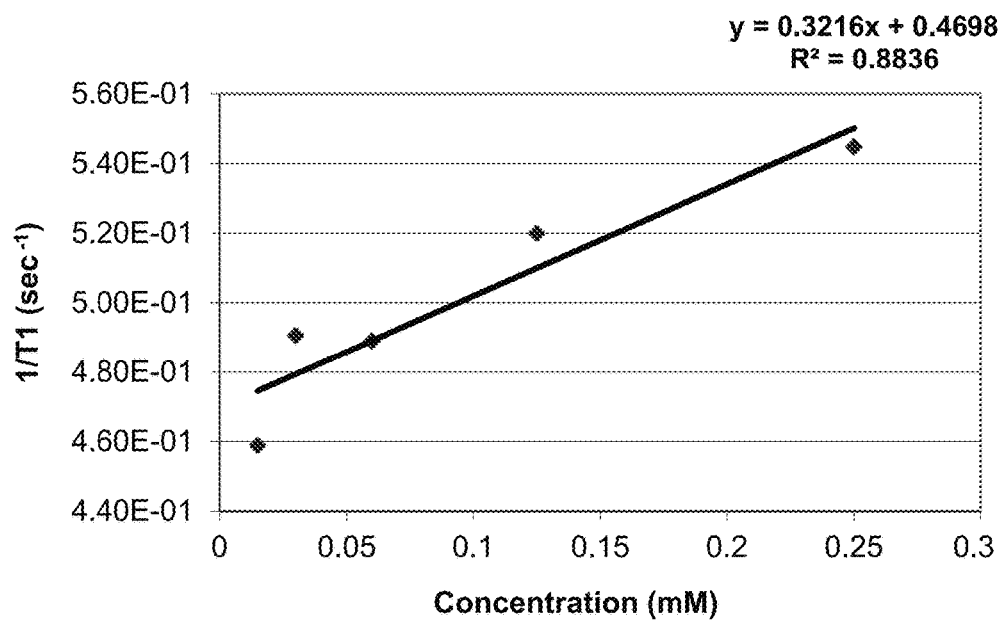
FIG. 6G shows a $T_1$ and FIG. 6H a $T_2$ relaxivity plot of $NaDyF_4$:$Yb^{3+}$/$NaGdF_4$:$Yb^{3+}$,$Er^{3+}$ NCs. Spin echo sequences were used to measure $T_1$ and $T_2$ relaxation time constant. The experimental paramaeters for $T_1$- and $T_2$-weighted imaging are TR/TE/NEX=400/8.9/16 and TR/TE/NEX=1500/41/16, respectively.
Figure 6H:
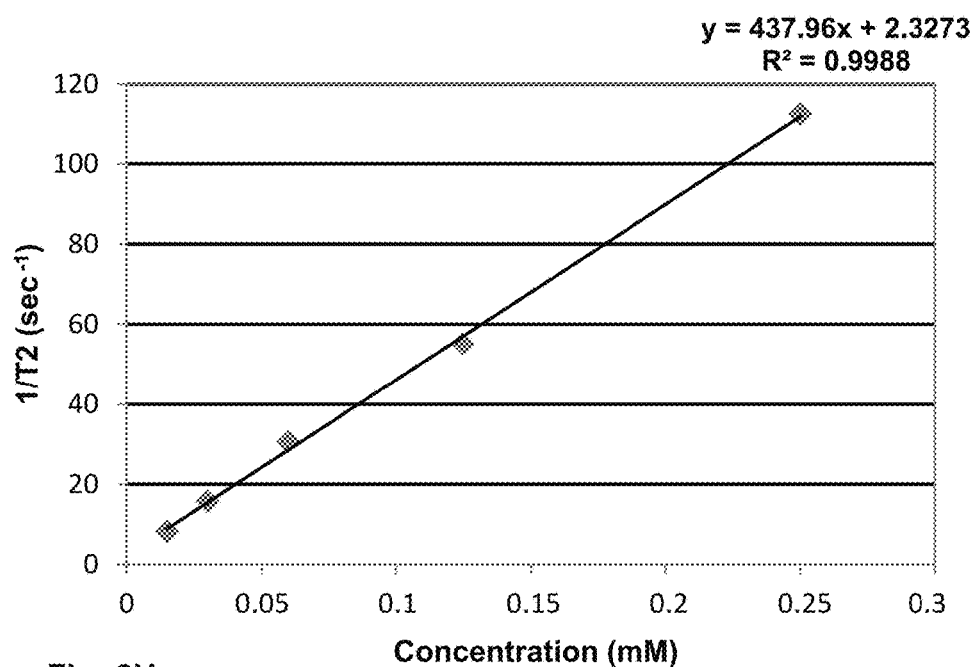
FIG. 6 depicts bright $T_1$-weighted MR images using a gradient echo sequence (A) dark $T_1$-weighted images using a spin echo sequence (B); $T_2$-weighted images of $NaDyF_4$:$Yb^{3+}$/$NaGdF_4$:$Yb^{3+}$,$Er^{3+}$ NCs at different concentrations (0, 0.0625, 0.125, 0.50, 1.00 mM (C); Dark $T_1$-weighted MR image (FIG. 6D); Dark $T_2$-weighted MR images (E); and bright $T_1$-weighted MR image using gradient echo sequence with an inversion pulse of $NaDyF_4$:$Yb^{3+}$/$NaGdF_4$:$Yb^{3+}$,$Er^{3+}$ NCs fixed 0.8% agarose, injected subcutaneously in a mouse model (FIG. 6F).

In vitro $T_1$- and $T_2$-weighted MR images of the $NaDyF_4$:$Yb^{3+}$/$NaGdF_4$:$Yb^{3+}$, $Er^{3+}$ NCs were measured as a function of metal concentration using a 7 T MRI system (FIG. 6A-6C). The NCs were rendered water-dispersible using an amphiphilic layer of cetyl trimethylammonium bromide (CTAB).[23] The NCs show excellent negative $T_2$ enhancement due to the presence of $Dy^{3+}$ ions (FIG. 6C). Interestingly, tunable positive and negative $T_1$ enhancement can be achieved by suitably employing a magnetization preparation module in a gradient echo (GE) or a spin echo (SE) sequence. In FIG. 6A, the images were acquired with a GE $T_1$-weighted sequence with a magnetization preparation (inversion pulse) module which exhibits a genuine $T_1$ contrast (positive enhancement). However, FIG. 6B shows $T_1$ weighted images acquired with a SE sequence without any preparation module, which clearly shows negative enhancement albeit the parameters were optimized to generate $T_1$ contrast. $r_1$ is determined to be 0.321 mM$^{-1}$ S$^{-1}$, while $r_2$ is determined to be 437.96 mM$^{-1}$ S$^{-1}$ as shown in FIG. 6G and FIG. 6H.

The SE based $T_2$ weighted experiments generate negative $T_2$ contrast due to the presence of $Dy^{3+}$ ions. $Dy^{3+}$ ions, having shorter electronic relaxation time (~0.5 ps) and higher magnetic moment (10.6$\mu_B$), have proved to efficiently induce $T_2$ contrast.[24] For example, Elst et al. examined Dy-DTPA derivatives as contrast agents in fields between 0.47 and 18.8 T.[25] Nanoparticles, such as $Dy_2O_3$, have also been investigated as $T_2$ contrast agents in high-field MRI (from 7 to 17.6 T).[26] Recently, we have reported ultrasmall $Dy_2O_3$ NCs as a positive $T_2$ contrast agent ($r_2$ of 2.12 mM$^{-1}$ s$^{-1}$).[26b] The relaxivity of $Dy^{3+}$ ions primarily originates from its magnetization and Curie Spin (CS) relaxation mechanism which becomes very dominant at high magnetic field.[24, 27] According to the CS relaxation mechanism, the induced Curie magnetic moment per $Dy^{3+}$ ion is given by: $\mu_C = \mu_S^2 B_0/3$ kT; where $\mu_S$ is the magnetic moment, k is Boltzmann's constant and T is the absolute temperature. This implies that induced magnetization of the $Dy^{3+}$ ions increases with external magnetic field and is proportional to square of the magnetic moment of $Dy^{3+}$ ions. The relaxivity, $r_2$ measured at 7 T MRI (437.96 mM$^{-1}$ s$^{-1}$) is resultant of a combined effect of the NPs magnetic moments and Curie Spin relaxation arises from $Dy^{3+}$ ions.

$Gd^{3+}$ ions, which have seven unpaired electrons, are known to have excellent $T_1$ enhancing properties due to their long electronic relaxation time.[11,28] In order to execute efficient exchange of magnetic fields with surrounding water protons to induce $T_1$ contrast, contrast agents are required to be in close contact with water molecules.[28,29] In the present study, $Gd^{3+}$ ions are doped in the outer layer of the nanocrystals, which remain in close contact with the surrounding water protons, and therefore capable of inducing $T_1$ relaxation. Interestingly, the current NCs generate $T_1$ negative contrast, which has never been reported to the best of our knowledge, in the normal SE based $T_1$-weighted experiments (in the absence of an inversion module). Contrast agents, including $Ln^{3+}$ ions, show both $T_1$ and $T_2$ relaxation properties at different extent. The $T_1$ contrast agents viz., Gd (III), demonstrate both $T_1$ and $T_2$ relaxation properties, but shortening of $T_1$ is dominated over that of $T_2$. This results in a hyperintense image within areas where the agents are taken up.[11] Thus, species with high $T_1$ values lend themselves to hypointense images.[11] The $r_1$ of NCs obtained from SE, is much smaller than that of other $T_1$ contrast agent, for example Gadovist (commercially Gd-based contrast agents, $r_1$=4.34 $mM^{-1}$ $S^{-1}$),[11] $Gd_2O_3$ NPs (8.8 $mM^{-1}$ $S^{-1}$ for size 2.2 nm and 4.4 $mM^{-1}$ $S^{-1}$ for size 4.6 nm),[30] ultrasmall $Gd_2O_3$ NRs (1.5 $mM^{-1}$ $S^{-1}$),[31] and $GdF_3$ (3.17 $mM^{-1}$ $S^1$),[32] indicating the $T_1$ relaxation of water is large in these NCs and hence capable of inducing negative contrast. The presence of $Dy^{3+}$ is inferred to affect the $T_1$ relaxivity induced by the $Gd^{3+}$ ions (due to the very short electronic relaxation time of $Dy^{3+}$ compared to $Gd^{3+}$ ions), hence leading to the current observation of negative $T_1$ contrast. Cheon and coworkers reported similar findings, that the coupling process between the electron spins of the $T_1$ contrast agent and nuclear spins of water is perturbed in the presence of additional magnetic field generated by $T_2$ contrast agent in close proximity.[13] One of the strategies to increase the relaxivity is to enhance the exchange rate of water between the NPs and the water in the bulk phase.[13] The water exchange rate of $Dy^{3+}$ ions is generally faster than that of the $Gd^{3+}$ ions. Therefore, the measured low $r_1$ could be attributed to the slow water exchange rate of $Gd^{3+}$ which is present in the outer layer of our NCs. In addition, the relaxivity measurements at high field (7 T) and the relatively larger size of NCs are another two reasons that may account for the lower $r_1$ of the current NCs. $Gd^{3+}$ is known to exhibit decreased relaxivity as magnetic field strength increases, which is consistent with our observation.[29b,33] Previous studies showed that smaller-size NCs, which have a higher surface area, showed a higher MR relaxivity due to easier magnetic exchange with surrounding water protons.[34] The rod-shaped NCs have relatively smaller surface area, thereby, a fairly large portion of the $Gd^{3+}$ ions are embedded inside the NCs which are less likely to contribute to the relaxation of water protons. Thus, the ionic relaxivity goes down due to a relatively thick shell around the $NaDyF_4$ NCs.

Despite a weak $T_1$ negative contrast, a stronger $T_1$ positive contrast was also obtained in a GE sequence when an inversion module was used at the start of the pulse sequence. The GE is generated by fast gradient reversal which allows minimum echo time and repetition time, and is characterized by rapid sampling time. Since the signal is detected rapidly during the recovery of the longitudinal magnetization, this sequence generates a good $T_1$ positive contrast.

To examine the feasibility of the nanocrystals (NCs) for in vivo application, the inventors performed subcutaneous injection of the NCs in a mouse model. It is apparent from the images that the NCs generate a negative $T_1$ and $T_2$ contrast for a SE sequence, in addition to positive $T_1$ contrast when using a GE with a preparation module consisting of an inversion pulse, with an inversion delay of 1800 ms (FIGS. 5D-5F). Thus, the NCs are capable of generating tunable $T_1$ and $T_2$ contrast by choosing appropriate MRI sequences. In addition to possessing the advantages of normal positive $T_1$ contrast agents for clear visualization of anatomic details and bright contrast for distinguishing from other pathogenic or biological condition, the current NCs also possess the advantages of negative $T_1$ CAs. One of the disadvantages of using positive $T_1$ CAs is the bright signal they generate which causes artifacts in the bowel lumen. This may be avoided if the signal can be tuned to a dark contrast. Generally the $T_2$-weighted experiment consumes more experimental time, because of large TR and TE, than the $T_1$-weighted experiments. Since our NCs generate negative $T_1$ enhancement (small TR and TE), they could find application in cases where negative contrast is desired within a limited experimental time. Therefore, depending on the tissue site of interest, the current NCs can be selectively tuned to visualize by bright or dark $T_1$- and $T_2$-weighted MRI contrast in order to achieve complementary information that cannot be obtained using single mode CAs. In addition, the image quality can also be improved, leading to more accurate diagnosis. The relaxivities of the current NCs may be optimized by varying the concentration of the dopants and/or introducing a physical barrier between the $Dy^{3+}$ and $Gd^{3+}$, so as to reduce the effect of $Dy^{3+}$ on $Gd^{3+}$.

Experimental

General: gadolinium (III) chloride hexahydrate (99.9%), ytterbium (III) chloride hexahydrate (99.9%), erbium (III) chloride hexahydrate (99.9%), dysprosium (III) chloride hexahydrate (99.9%), sodium fluoride (99.9%), sodium oleate, octadecence, oleic acid, cetyl trimethylammonium bromide were purchased from Sigma-Aldrich and used without further purification. Ethanol, Chloroform (AR grade) was purchased from VWR International Ltd.

Synthesis of $NaDyE_4$:$Yb^{3+}$ Seed NCs

Thermal decomposition of lanthanide-oleate complex was used to synthesize desired NCs. Briefly, dysprosium chloride hexahydrate (0.3016 g, 0.8 mmol) and ytterbium chloride hexahydrate (0.0775 g, 0.2 mmol) were dissolved in a solvent mixture composed of ethanol (7 ml), distilled water (7 ml) and hexane (15 ml). The resulting solution was heated to 70° C., an excess of sodium oleate (0.6089 g, 2 mmol) was added into the solution and reacted at 70° C. for 4 h. When the reaction was completed, the upper organic layer containing the lanthanide-oleate complex was washed with distilled water in a reparatory funnel three times. After washing, a solid waxy complex was formed after evaporating off hexane. The lanthanide-oleate complexes were then dissolved in oleic acid and 1-octadecane (15 ml/15 ml) at room temperature. After adding sodium fluoride (0.21 g, 5 mmol) into the flask, the solution was degassed under vacuum with magnetic stirring for 30 min. After degassing to remove residual water and oxygen, the flask was purged with $N_2$ gas and then the reaction mixture was heated to 300° C. and kept at that temperature for 2 h. The resulting solution was cooled to room temperature and the NCs were obtained after washing with ethanol and hexane three times. Finally, the NCs were dispersed in hexane.

Synthesis of $NaDyF_4$:$Yb^{3+}$/$NaGdF_4$:$Yb^{3+}$,$Er^{3+}$ NRs

The seed NCs, Gd-oleate complex (0.8013 g, 0.8 mmol), Yb-oleate complex (0.1831 g, 0.18 mmol), Er-oleate complex (0.0202 g, 0.02 mmol), sodium fluoride (0.21 g, 5 mmol), oleic acid (15 ml) with octadecene (15 ml) were mixed in a three-necked reaction flask. The solution was degassed under vacuum with magnetic stirring for 30 min. Then, the flask was purged with $N_2$ and heated to 300° C., and kept at this temperature for 2 h under vigorous stirring to form the final NRs. After the reaction, the solution was cooled down to room temperature, and washed with ethanol and hexane for three times. The NRs were obtained after washing and they were readily dispersed in organic solvents such as hexane, cyclohexane, toluene and chloroform.

Surface Functionalization of $NaDyF_4:Yb^{3+}/NaGdF_4:Yb^{3+}$, $Er^{3+}$ NRs

In a typical synthesis procedure, an aqueous solution (15 ml) containing cetyl trimethylammonium bromide (0.4 g) was firstly prepared. The solution was sonicated until a transparent solution formed. Addition of the $NaDyF_4:Yb^{3+}/NaGdF_4:Yb^{3+}$, $Er^{3+}$ NRs (1 mmol) in chloroform (5 ml) suspension into the aqueous solution under vigorous stirring resulted in the formation of an oil-in-water microemulsion. Evaporation of chloroform during heating (40-80° C., ~10 min) transfers the $NaDyF_4:Yb^{3+}/NaGdF_4:Yb^{3+}$, $Er^{3+}$ NRs into the aqueous phase.

Characterization of Nanocrystals (NCs)

Transmission Electron Microscopy.

The transmission electron microscopy (TEM) images and selected area electron diffraction (SAED) patterns were acquired using a JEOL JEM-2100F microscope operating at 200 kV. Two drops of NC dispersion were placed onto a carbon film supported on a 200 mesh copper grid (3 mm in diameter) and allowed to dry in air at room temperature. The carbon grid with NCs sample was then mounted into the vacuum chamber for imaging and SAED.

Powder X-ray Diffraction.

Approximately 50 mg of the NCs sample was pressed gently in an agate mortar to break up lumps. The powdery samples were then spread evenly onto a zero background holder. Step-scan X-ray powder diffraction data were collected over the range of 2θ range of 10-80° on a D8 Advance Bruker powder X-ray diffractometer with Cu Kα (operated at 40 kV, 40 kA) radiation. The scanning step size was 0.02° 2 θ with a counting time of 1 s per step.

Energy Dispersive X-Ray Spectroscopy.

Energy-Dispersive X-Ray (EDX) spectroscopy was done using a high resolution transmission electron microscope (JEOL, JEM 2100-F, Japan) operating at 200 kV and EDS (EDAX, AMETEK, USA, system resolution: 135 eV). A few drops of NCs dispersion were put onto a holey carbon film supported on a 200 mesh copper grid (3 mm in diameter) and allowed to dry in air at room temperature. The carbon grid with sample was then mounted into the vacuum chamber for elemental compositional analysis.

Fluorescence Studies.

NCs were dispersed in cyclohexane in a standard square quartz cuvette at room temperature and their photoluminescence spectra were obtained using a Shimadzu RF-5301 PC Spectrofluorometer fitted with a 150 W xenon lamp as the excitation source with a resolution of 1 nm.

MRI Relaxometry Studies.

The $T_1$ and $T_2$-weighted images were obtained on a 7 T Bruker ClinScan MRI system. All samples were dissolved in double distilled water. The repetition time (TR) and echo time (TE) were optimized for $T_1$ or $T_2$. Other relevant acquisition parameters are: number of acquisitions=16, field of view=39 mm, slice thickness=1 mm. All experiments were performed in 1% agarose medium.

In these Examples the inventors have demonstrated (1) a new strategy of combining both UC fluorescence imaging and tunable $T_1$-$T_2$ dual-mode MRI contrast properties within a single NC (2) of which all functionalities arise solely from lanthanide ions (illustrated in FIG. 1a).

(3) $Dy^{3+}$ ions induce good $T_2$ negative contrast. The $NaDyF_4:Yb^{3+}$ seed particles were first prepared, which underwent further growth in a second reaction in the presence of $Gd^{3+}$, $Yb^{3+}$ and $Er^{3+}$ to form nanorods.

(4) To circumvent the "poisoning" or quenching by $Dy^{3+}$ ions, we chose ytterbium ($Yb^{3+}$) ions as the co-dopant sensitizers. $Yb^{3+}$ ions possess single excited state at 980 nm. More importantly, the absorption cross-section of excited $Yb^{3+}$ ions is significantly greater than many of the excited states of other lanthanides with similar energy levels, rendering the UC or energy transfer process more efficient.[35] Fluoride hosts have been demonstrated to possess strong and efficient up-conversion due to their high chemical stability and low photon energies (~350 $cm^{-1}$).[36]

(5) Gadolinium ($Gd^{3+}$) ions on the outer layer of NCs efficiently induce electron-nuclear dipolar interactions with the surrounding water protons, hence shortening the longitudinal relaxation time ($T_1$) and generating $T_1$ MRI contrast.

(6) The resultant NCs demonstrate simultaneous up-conversion luminescence and tunable $T_1/T_2$ contrast enhancement in MRI, this first of its kind, making them good candidates as dual-functional optical and MR imaging contrast agents.

REFERENCES (1) (a) Kim, J.; Piao, Y.; Hyeon, T. *Chem. Soc. Rev.* 2009, 38, 372(b) Louie, A. *Chemical Review* 2010, 110, 3146.

(2) (a) Nahrendorf, M., Sosnovik, D. E., Weissleder, R. *Basic Research in Cardiology* 2008, 103, 87(b) Prinzen, L., Miserus, Robbert-Jan J. H. M., Dirksen, Anouk, Hackeng, Tilman M., Deckers, Niko, Bitsch, Nicole J., Megens Douma, Kim, Heemskerk, Johan W., Kooi, M. Eline, Frederik, Peter M., Slaaf, Dick W., van Zandvoort, Marc A. M. J., Reutelingsperger, Chris P. M. *Nano Letters* 2006, 7, 93(c) Prinzen, L.; Miserus, R. J. J. H. M.; Dirksen, A.; Hackeng, T. M.; Deckers, N.; Bitsch, N. J.; Megens; Douma, K.; Heemskerk, J. W.; Kooi, M. E.; Frederik, P. M.; Slaaf, D. W.; van Zandvoort, M. A. M. J.; Reutelingsperger, C. P. M. *Nano Lett.* 2006, 7, 93.

(3) (a) Frullano, L.; Meade, T. J. *J. Biol. Inorg. Chem.* 2007, 12, 939(b) Basilion, J. P., S. Yeon, R. Botnar *Current Topics in Development Biology* 2005, 70, 1.

(4) (a) Sharma, P., Brown, S., Walter, G., Santra, S., Moudgil, B. *Advances in Colloid and Interface Science* 2006, 123-126, 471(b) Shen, J., Sun, L. D., Yan, C. H. *Dalton Transactions* 2008, 5687.

(5) Jennings, L. E.; Long, N. J. *Chemical Communications* 2009, 24, 3511.

(6) Ble, F. X.; Schmidt, P.; Cannet, C.; Kneuer, R.; Karmouty-Quintana, H.; Bergmann, R.; Coote, K.; Danahay, H.; Zurbruegg, S.; Gremlich, H. U.; Beckmann, N. *Magn. Reson. Med.* 2009, 62, 1164.

(7) Li, Z.; Zhang, Y.; Shuter, B.; Muhammad Idris, N. *Langmuir* 2009, 25, 12015.

(8) Wang, D.; He, J.; Rosenzweig, N.; Rosenzweig, Z. *Nano Lett.* 2004, 4, 409.

(9) Huang, C. C.; Su, C. H.; Li, W. M.; Liu, T. Y.; Chen, J. H.; Yeh, C. S. *Adv. Funct. Mater* 2009, 19, 249.

(10) Lauffer, R. B. *Chem. Rev.* 1987, 87, 901.

(11) Bottrill, M.; Kwok, L.; Long, N. J. *Chemical Society Reviews* 2006, 35, 557.

(12) Bae, K. H.; Kim, Y. B.; Lee, Y.; Hwang, J. Y.; Park, H.; Park, T. G. *Bioconjugate Chem.* 2010, 21, 505.
(13) Choi, J. S.; Lee, J. H.; Shin, T. H.; Song, H. T.; Kim, E. Y.; Cheon, J. *J. Am. Chem. Soc.* 2010, 132, 11015.
(14) Hu, F.; Jia, Q.; Li, Y.; Gao, M. *Nanotechnology* 2011, 22.
(15) Seo, W. S.; Lee, J. H.; Sun, X.; Suzuki, Y.; Mann, D.; Liu, Z.; Terashima, M.; Yang, P. C.; McConnell, M. V.; Nishimura, D. G.; Dai, H. *Nat Mater* 2006, 5, 971.
(16) Wang, F.; Tan, W. B.; Zhang, Y.; Fan, X.; Wang, M. *Nanotechnology* 2006, 17, R1.
(17) Auzel, F. *Chem. Rev.* 2004, 104, 139.
(18) Gong, J.; Zhao, H.; Liu, T.; Ling, R.; Xu, J. *Clin. Imaging* 2009, 33, 361.
(19) Mai, H. X.; Zhang, Y. W.; Si, R.; Yan, Z.-G.; Sun, L. D.; You, L. P.; Yan, C. H. *J. Am. Chem. Soc.* 2006, 128, 6426.
(20) (a) Boyer, J. C.; Cuccia, L. A.; Capobianco, J. A. *Nano Lett.* 2007, 7, 847(b) Boyer, J. C.; Vetrone, F.; Cuccia, L. A.; Capobianco, J. A. *J. Am. Chem. Soc.* 2006, 128, 7444.
(21) Yasuo S., Y. F. *Japanese Journal of Applied Physics* 1971, 10, 891.
(22) Wang, F.; Liu, X. *Chemical Society Reviews* 2009, 38, 976.
(23) Fan, H.; Leve, E. W.; Scullin, C.; Gabaldon, J.; Tallant, D.; Bunge, S.; Boyle, T.; Wilson, M. C.; Brinker, C. J. *Nano Lett.* 2005, 5, 645.
(24) Viswanathan, S.; Kovacs, Z.; Green, K. N.; Ratnakar, S. J.; Sherry, A. D. *Chem. Rev.* 2010, 110, 2960.
(25) Luce Vander Elst, A. R., Pierre Gillis, Sophie Laurent, Francois Botteman, Jeff W. M. Bulte, and Robert N. Muller *Magn. Reson. Med.* 2002, 47, 1121.
(26) (a) Norek, M.; Kampert, E.; Zeitler, U.; Peters, J. A. *Journal of the American Chemical Society* 2008, 130, 5335(b) Das, G. K.; Zhang, Y.; D'Silva, L.; Padmanabhan, P.; Heng, B. C.; Chye Loo, J. S.; Selvan, S. T.; Bhakoo, K. K.; Yang Tan, T. T. *Chem. Mater.* 2011, 23, 2439.
(27) Norek, M.; Peters, J. A. Progress in *Nuclear Magnetic Resonance Spectroscopy* 2011, 59, 64.
(28) (a) Caravan, P. *Chemical Society Reviews* 2006, 35, 512(b) Caravan, P., Ellison, Jeffrey J., McMurry, Thomas J., Lauffer, Randall B. *Chem. Rev.* 1999, 99, 2293.
(29) (a) Hyon Bin Na, J. H. L., Kwangjin An, Yong Il Park, Mihyun Park, In Su Lee, Do-Hyun Nam, Sung Tae Kim, Seung-Hoon Kim, Sang-Wook Kim, Keun-Ho Lim, Ki-Soo Kim, Sun-Ok Kim, and Taeghwan Hyeon *Angew. Chem. Int. Ed.* 2007, 46, 5397(b) Helm, L. Future Medicinal Chemistry 2010, 2, 385(c) Hermann, P.; Kotek, J.; Kubíček, V.; Lukeš, I. *Dalton Transactions* 2008, 3027.
(30) Bridot, J. L.; Faure, A. C.; Laurent, S.; Rivire, C.; Billotey, C.; Hiba, B.; Janier, M.; Josserand, V.; Coll, J. L.; Vander Elst, L.; Muller, R.; Roux, S.; Perriat, P.; Tillement, O. *J. Am. Chem. Soc.* 2007, 129, 5076.
(31) Das, G. K.; Heng, B. C.; Ng, S. C.; White, T.; Loo, J. S. C.; D'Silva, L.; Padmanabhan, P.; Bhakoo, K. K.; Selvan, S. T.; Tan, T. T. Y. *Langmuir* 2010, 26, 8959.
(32) Evanics, F.; Diamente, P. R., van Veggel, F. C. J. M., Stanisz, G. J., Prosser, R. S. *Chem. Mater.* 2006, 18, 2499.
(33) Gossuin, Y.; Hocq, A.; Vuong, Q. L.; Disch, S.; Hermann, R. P.; Gillis, P. *Nanotechnology* 2008, 19, 475102.
(34) Jun, Y. W.; Lee, J. H.; Cheon, J. *Angew. Chem. Int. Ed.* 2008, 47, 5122.
(35) (a) Ralph A, H. J. Lumin. 1970, 1-2, 778(b) J. C. Boyer, F. V., J. A. Capobianco, A. Speghini, M. Bettinelli *Chem. Phys. Lett.* 2004, 390, 403.
(36) (a) Boyer, J. C.; Gagnon, J.; Cuccia, L. A.; Capobianco, J. A. *Chem. Mater.* 2007, 19, 3358(b) Li, Z., Zhang, Y., Jiang, S. *Advanced Materials* 2008, 20, 4765.
(37) Liu, B., et al., *J. Am. Chem. Soc.* 2004, 126, 4076.
(38) Querner, C., et al., *Chem. Mater.* 2006, 18, 4817.
(39) Hwang, I., et al., *J. Am. Chem. Soc.* 2007, 129, 4170.
(40) X. Peng, J. Chen, J. A. Misewichb, S. S. Wong, *Chem. Soc. Rev.* 2009, 38, 1076.
(41) H. Sami, A. K. Maparu, A. Kumar, S. Sivakumar, *PLOS ONE* 2012, 7, 5, e36195.
(42) L. L. Li, R. Zhang, L. Yin, W. Qin, P. R. Selvin, Y. Lu., *Angew Chem Int Ed Engl.* 2012, 51, 25, 6121.

What is claimed is:

1. A nanoparticulate composite comprising a first and a second layer,
    wherein the first layer comprises one or more metals and one or more dopants, wherein the one or more metals comprise dysprosium (III) as a paramagnetic metal, and the one or more dopants comprise an $Yb^{3+}$ dopant; and
    wherein the second layer comprises gadolinium (III), being an oxide, a fluoride or a phosphate, and an $Yb^{3+}$ dopant and an $Er^{3+}$ dopant.

2. The nanoparticulate composite of claim 1, wherein the one or more metals comprised in the first layer are an oxide or a fluoride.

3. The nanoparticulate composite of claim 1, wherein the one or more metals comprised in the first layer comprise one or more of $Dy_2O_3$, $DyF_3$, $NaDyF_4$, $LiDyF_4$, and $KDyF_4$.

4. The nanoparticulate composite of claim 1, wherein the second layer comprises one or more of $GdF_3$, $Gd_2O_3$, $GdPO_4$, $LiGdF_4$, $NaGdF_4$, and $KGdF_4$.

5. The nanoparticulate composite of claim 1, wherein the second layer comprises one or more further lanthanide dopants.

6. The nanoparticulate composite of claim 5, wherein the further dopant comprised in the second layer is one or more dopants of $Tm^{3+}$, and $Ho^{3+}$.

7. The nanoparticulate composite of claim 1, being a core/shell nanocrystal or a heterodimer.

8. The nanoparticulate composite of claim 7, being a core/shell nanocrystal, wherein the first layer defines the core, and the second layer defines the shell.

9. The nanoparticulate composite of claim 8, comprising a surfactant immobilized on the core/shell nanocrystal surface.

10. A contrast agent comprising one or more nanoparticulate composites according to claim 1.

11. The contrast agent of claim 10, being a $T_1$-$T_2$ dual mode MRI contrast agent.

12. The contrast agent of claim 10, further being configured, upon exposure to a first wavelength $\lambda_1$ of radiation, to generate a second wavelength $\lambda_2$ of radiation having a higher energy than the first wavelength $\lambda_1$.

13. A method of performing magnetic resonance imaging or upconversion fluorescence imaging, the method comprising contacting a nanoparticulate composite of claim 1 with a sample and performing magnetic resonance imaging or upconversion fluorescence imaging on the sample.

14. The method of claim 13, wherein the sample is an organ or a tissue of a mammal.

15. The method of claim 13, wherein the sample is exposed to a magnetic field applied for magnetic resonance imaging.

* * * * *